US012746229B2

(12) United States Patent
Dai et al.

(10) Patent No.: US 12,746,229 B2
(45) Date of Patent: Sep. 29, 2026

(54) ORAL FORMULATIONS AND USES THEREOF

(71) Applicant: INVENTISBIO CO., LTD., Shanghai (CN)

(72) Inventors: Xing Dai, Short Hills, NJ (US); Xiaomei Wang, Shanghai (CN); Yanqin Liu, Shanghai (CN); Yueheng Jiang, Shanghai (CN); Yaolin Wang, Shanghai (CN)

(73) Assignee: INVENTISBIO CO., LTD., Shanghai (CN)

( * ) Notice: Subject to any disclaimer, the term of this patent is extended or adjusted under 35 U.S.C. 154(b) by 719 days.

(21) Appl. No.: 18/010,735

(22) PCT Filed: Jun. 18, 2021

(86) PCT No.: PCT/CN2021/100806
§ 371 (c)(1),
(2) Date: Dec. 15, 2022

(87) PCT Pub. No.: WO2021/254471
PCT Pub. Date: Dec. 23, 2021

(65) Prior Publication Data

US 2023/0263782 A1 Aug. 24, 2023

(30) Foreign Application Priority Data

Jun. 19, 2020 (WO) ................ PCT/CN2020/097036

(51) Int. Cl.

| | |
|---|---|
| ***A61K 31/437*** | (2006.01) |
| ***A61K 9/16*** | (2006.01) |
| ***A61K 9/20*** | (2006.01) |
| ***A61K 45/06*** | (2006.01) |
| ***A61K 47/18*** | (2017.01) |

(52) U.S. Cl.
CPC .......... *A61K 31/437* (2013.01); *A61K 9/1694* (2013.01); *A61K 9/2013* (2013.01); *A61K 9/2018* (2013.01); *A61K 9/2027* (2013.01); *A61K 9/2054* (2013.01); *A61K 45/06* (2013.01); *A61K 47/18* (2013.01)

(58) Field of Classification Search
CPC ...... A61K 31/437; A61K 45/06; A61K 47/18; A61K 9/1623; A61K 9/1635; A61K 9/1652; A61K 9/1694; A61K 9/2013; A61K 9/2018; A61K 9/2027; A61K 9/2054; A61K 9/5026; A61P 35/00
See application file for complete search history.

(56) References Cited

U.S. PATENT DOCUMENTS

| | | | | |
|---|---|---|---|---|
| 10,647,724 | B2 * | 5/2020 | Dai | C07D 495/04 |
| 11,241,418 | B2 * | 2/2022 | Dai | A61K 45/06 |
| 2020/0197375 | A1 * | 6/2020 | Dai | A61K 31/4375 |

FOREIGN PATENT DOCUMENTS

| | | |
|---|---|---|
| CN | 105229004 | 1/2016 |
| CN | 108864080 | 11/2018 |
| CN | 109311870 | 2/2019 |
| WO | 2017/136688 | 8/2017 |
| WO | 2018/130124 | 7/2018 |
| WO | 2020/132785 | 7/2020 |

OTHER PUBLICATIONS

Cecil Textbook of Medicine, 20th Ed., vol. 1 (Year: 1997).*
Wu et. al., Small-molecule inhibitors, immune checkpoint inhibitors, and more: FDA-approved novel therapeutic drugs for solid tumors from 1991 to 2021; Journal of Hematology & Oncology, 15, 143 (Year: 2022).*
International Search Report for PCT/CN2021/100806 dated Sep. 18, 2021, 4 pages.
Written Opinion of the ISA for PCT/CN2021/100806 dated Sep. 18, 2021, 9 pages.

* cited by examiner

*Primary Examiner* — Jeffrey H Murray
*Assistant Examiner* — Daniel John Burkett
(74) *Attorney, Agent, or Firm* — NIXON & VANDERHYE, PC

(57) ABSTRACT

Provided herein are compounds, salts, crystalline forms, and pharmaceutical compositions that are related to Selective Estrogen Receptor Degraders, as well as methods of preparing the same. Also provided herein are methods of using the compounds, salts, crystalline forms, and pharmaceutical compositions for the treatment of diseases or disorders, such as breast cancer.

20 Claims, 13 Drawing Sheets

ORAL FORMULATIONS AND USES THEREOF

CROSS-REFERENCE TO RELATED APPLICATIONS

This application is the U.S. national phase of International Application No. PCT/CN2021/100806 filed Jun. 18, 2021 which designated the U.S. and claims priority to PCT/CN2020/097036 filed Jun. 19, 2020, the entire contents of each of which are hereby incorporated by reference.

BACKGROUND

Field of the Disclosure

In various embodiments, the present disclosure generally relates to novel salts of Selective Estrogen Receptor Degraders (SERDs), pharmaceutical compositions comprising the same, and methods of preparation and use thereof.

Background Art

Breast cancer is the most common cause of death for women worldwide. Majority of breast cancer (~80%) depends on the signaling pathway mediated by the estrogen receptor (ER) for growth. Therefore, targeting the ER or its signaling pathway remains to be the key in development of drug for treating breast cancer. Estrogen receptors (including ERα and ERβ) are a group of receptors that are activated by the hormone estrogen (17β-estradiol). Current therapy for ER positive (ER+) breast cancer including agents that inhibit the ER activity through direct binding to the ligand binding domain of the receptor (e.g., tamoxifen); blocking the synthesis of estrogen (e.g., aromatase inhibitor such as anastrozole and letrozole); or inducing the degradation of ER (e.g., fulvestrant).

Drugs that inhibit estrogen receptor or block the production of estrogens are commonly used in the treatment and management of ER+ breast cancer and other hormone-dependent cancers. However, drug resistance remains a challenge in breast cancer treatment, particularly treatment of cancers in advanced stages.

BRIEF SUMMARY

Selective Estrogen Receptor Degraders (SERD) are a class of small molecules that bind to the estrogen receptor, resulting in degradation of the estrogen receptor. Studies showed that SERDs are specifically useful in treating cancers that are resistant to other drugs such as tamoxifen and/or aromatase inhibitors (McDonnell et al., J. Med. Chem. 2015, 58, 4883-4887). Fulvestrant is a SERD that has been approved for treatment of ER+ breast cancer. However, fulvestrant is metabolized quickly and is administered by intramuscular injection monthly, which limit the effective degradation of ER (~50% ER degradation in clinical samples) compared to the complete ER degradation seen in in vitro study. Recently, ER mutations have been detected in biopsy samples from breast cancer patients who have developed resistance to treatment of aromatase inhibitor. These mutations are mostly frequently occurring at amino acid 537 and 538 within the ligand binding domain of ER. Interestingly, these mutated ERs still bind to and are inhibited by both tamoxifen and fulvestrant to some degree (Li et al., 2013 Cell Reports 4, 1116-1130; Toy et al., 2013, 45, 1439-1445; Robinson et al., Nature Genetics 2013, 45, 1446-1451). It has also been shown that fulvestrant can still effectively degrade the mutated Try537Ser ER protein. Compounds targeting the ER degradation similar to fulvestrant could effectively degrade the mutated ER protein as well and are useful in treating breast cancer patients that developed resistance to aromatase inhibitor.

WO2017/136688 describes various SERDs as useful for treating various diseases or disorders such as breast cancer, in particular ER+ breast cancer, and/or other ER related diseases. In various embodiments, the present disclosure is directed to certain salts of SERDs, for example, in a crystalline form and/or as a substantially pure isolated salt, pharmaceutical compositions comprising the same, methods of preparing the same, and methods of using the same.

Certain specific embodiments of the present disclosure are directed to amine salts of (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid ("Compound FA"). In some embodiments, the amine salt is a meglumine salt, trialkyl amine salt, lysine salt, arginine salt, tromethamine salt, choline salt, or ammonium salt. In some embodiments, the present disclosure provides a meglumine salt of Compound FA. In some embodiments, the meglumine salt of Compound FA can be in the form of Form I, II, or III as defined herein. In some embodiments, the present disclosure provides a lysine salt of Compound FA. In some embodiments, the lysine salt of Compound FA is an L-lysine salt (1:1 molar ratio). In some embodiments, the L-lysine salt can be in the form of Form A as defined herein. In some embodiments, the present disclosure provides a trialkyl amine salt of Compound FA, such as diisopropylethyl amine salt. In some embodiments, the trialkylamine salt is in a crystalline form. In some embodiments, the present disclosure also provides methods for preparing the amine salts of Compound FA. Typically, the method comprises dissolving Compound FA in a suitable solvent to form a Compound FA solution and then adding appropriate amine into the solution.

The salts of the present disclosure, such as the amine salts herein (e.g., any of the crystalline forms described herein) can be included in a pharmaceutical composition, for example, for the treatment of a proliferative disease or disorder such as breast cancer, in particular ER+ breast cancer, and/or diseases or disorders associated with ER. In some embodiments, the pharmaceutical composition can comprise a therapeutically effective amount of any one or more of the salts of the present disclosure. For example, in some specific embodiments, the active ingredient in the pharmaceutical composition can comprise, consist essentially of, or consist of the meglumine salt of Compound FA in Form I. In some specific embodiments, the active ingredient in the pharmaceutical composition can comprise, consist essentially of, or consist of the meglumine salt of Compound FA in Form II. In some specific embodiments, the active ingredient in the pharmaceutical composition can comprise, consist essentially of, or consist of the meglumine salt of Compound FA in Form III. In some specific embodiments, the active ingredient in the pharmaceutical composition can comprise, consist essentially of, or consist of the meglumine salt of Compound FA in Form I, amorphous form, or a mixture thereof. The salts herein, such as the amine salts herein (e.g., any of the crystalline forms described herein) can be used alone, in combination with each other, or with an additional pharmaceutical agent, e.g., described herein.

Compound FA is practically insoluble in water. This leads to a low rate of dissolution of Compound FA in aqueous media (including gastrointestinal fluids), which results in inadequate bioavailability after oral ingestion. In some embodiments, the amine salts herein can have a better aqueous solubility than that of Compound FA. Further, in some embodiments, the pharmaceutical compositions herein comprises micronized amine salts of Compound FA as well as a surfactant, which leads to a faster dissolution and better overall oral pharmacokinetic profile.

The pharmaceutical compositions described herein can be formulated for any suitable routes of administration. In some embodiments, the pharmaceutical composition can be formulated for oral administration. For example, in some embodiments, the pharmaceutical composition can be a tablet or a capsule.

Some specific embodiments of the present disclosure are directed to pharmaceutical compositions comprising a meglumine salt of Compound FA in an amount equivalent to about 5 mg to about 1.2 gram, such as about 10 mg to about 800 mg, of Compound FA. In some embodiments, the pharmaceutical composition comprises the meglumine salt of Compound FA in crystalline form I. In some embodiments, the pharmaceutical composition further comprises the meglumine salt of Compound FA in an amorphous form. In some embodiments, the pharmaceutical composition further comprises a surfactant, such as sodium lauryl sulfate. In some embodiments, the pharmaceutical composition further comprises a diluent, e.g., microcrystalline cellulose and/or mannitol. In some embodiments, the pharmaceutical composition further comprises a binder, e.g., povidone, such as povidone K30. In some embodiments, the pharmaceutical composition further comprises a disintegrant, e.g., crospovidone, such as crospovidone XL-10. In some embodiments, the pharmaceutical composition further comprises a lubricant. In some embodiments, the pharmaceutical composition is in a unit dosage form. In some embodiments, the pharmaceutical composition is an immediate release formulation. In some embodiments, the pharmaceutical composition is a tablet or a capsule, such as a coated tablet.

Some specific embodiments of the present disclosure are directed to tablets comprising a meglumine salt of Compound FA. In some embodiments, the tablet comprises a) the meglumine salt of Compound FA in an amount of about 10% to about 80% by weight; b) a surfactant in an amount of about 0.1% to about 10% by weight; c) a diluent in an amount of about 15% to about 70% by weight; d) a binder in an amount of about 0.1% to about 10% by weight; e) a disintegrant in an amount of about 0.1% to about 10% by weight; and f) a lubricant in an amount of about 0.1% to about 5% by weight. In some embodiments, the pharmaceutical composition comprises the meglumine salt of Compound FA in crystalline form I. In some embodiments, the pharmaceutical composition further comprises the meglumine salt of Compound FA in an amorphous form. Suitable amounts of the meglumine salt of Compound FA, the types and amounts of the surfactant, diluent, binder, disintegrant, and lubricant, for the tablets herein include any of those described herein in any combination. In some embodiments, the tablet is in a unit dosage form. In some embodiments, the tablet is an immediate release formulation. In some embodiments, the tablet further comprising a coating, e.g., with a coating weight gain of about 1% to about 5%.

Some specific embodiments of the present disclosure are directed to granules comprising a meglumine salt of Compound FA. In some embodiments, the granule comprises a) the meglumine salt of Compound FA in an amount of about 10% to about 80% by weight; b) a surfactant in an amount of about 0.1% to about 10% by weight; c) a diluent in an amount of about 15% to about 70% by weight; d) a binder in an amount of about 0.1% to about 10% by weight; and e) a disintegrant in an amount of about 0.1% to about 10% by weight. In some embodiments, the granule comprises the meglumine salt of Compound FA in crystalline form I. In some embodiments, the granule further comprises the meglumine salt of Compound FA in an amorphous form. Suitable amounts of the meglumine salt of Compound FA, the types and amounts of the surfactant, diluent, binder, and disintegrant, for the granules herein include any of those described herein in any combination. In some embodiments, the granule can be used for preparing a tablet herein. In some embodiments, the granule can be used for preparing a capsule formulation.

Some specific embodiments are also directed to methods of preparing the pharmaceutical composition herein. In some embodiments, the method comprises wet granulating a mixture of a meglumine salt of Compound FA, surfactant, diluent, binder, and disintegrant to form wet granules. In some embodiments, the pharmaceutical composition can also be prepared by dry granulating or direct blending a meglumine salt of Compound FA with one or more excipients prior to encapsulation or compression. In some embodiments, the method further comprises drying the wet granules to form dried granules, e.g., with fluid bed drying to no more than 3% water content. In some embodiments, the method further comprises dry milling the dried granules to form dry milled granules. In some embodiments, the method further comprises blending the dry milled granules with an extra-granular binder and a lubricant to form lubricated granules. In some embodiments, the method further comprises compressing the lubricated granules into a tablet core. In some embodiments, the method further comprises film coating the tablet core to form a coated tablet. In some embodiments, the mixture used for wet granulating comprises the meglumine salt of Compound FA in crystalline form I. In some embodiments, the mixture used for wet granulation further comprises the meglumine salt of Compound FA in an amorphous form. Suitable amounts of the meglumine salt of Compound FA, the types and amounts of the surfactant, diluent, binder, disintegrant, and lubricant, for the methods herein include any of those described herein in any combination.

In some embodiments, the present disclosure provides a pharmaceutical composition that includes micronized meglumine salt of Compound FA (e.g., described herein), which for example can have a $D_{90}$ less than 500 μm. Other suitable ingredients include any of those described herein as suitable in any combinations. In some embodiments, the present disclosure provides a pharmaceutical composition that includes a meglumine salt of Compound FA (e.g., described herein) and a surfactant (e.g., described herein), for example, sodium lauryl sulfate. In some embodiments, the pharmaceutical composition includes a micronized meglumine salt of Compound FA (e.g., described herein) and a surfactant (e.g., described herein), for example, sodium lauryl sulfate. In some embodiments, the micronized meglumine salt of Compound FA can have a $D_{90}$ less than 500 μm. Other suitable ingredients include any of those described herein as suitable in any combinations.

Certain embodiments of the present disclosure are directed to methods of using the salts of the present disclosure, such as the amine salts herein (e.g., any of the crystalline forms described herein) and/or pharmaceutical compositions herein (e.g., any of the tablets or granules described herein) for treating diseases or disorders associated with ER, such as ER positive breast cancer or a gynecological disease associated with ER. The methods described herein are not limited to any specific routes of administration. For example, in some embodiments, the administration can be oral administration. In some embodiments, the methods herein can further include administering an additional pharmaceutical agent (e.g., described herein) to the subject in need thereof. In some embodiments, the additional pharmaceutical agent can be administered concurrently or sequentially in any order.

BRIEF DESCRIPTION OF THE DRAWINGS/FIGURES

FIG. 1A shows a representative X-ray powder diffraction (XRPD) spectrum of crystalline form I of the meglumine salt of Compound FA. FIG. 1B shows a representative thermogravimetric analysis (TGA) and differential scanning calorimetry (DSC) analysis of crystalline form I of the meglumine salt of Compound FA. FIG. 1C presents XRPD spectra showing that Form I remained unchanged after storage under the condition of 25° C./92.5% RH for 10 days.

Figure 5A:
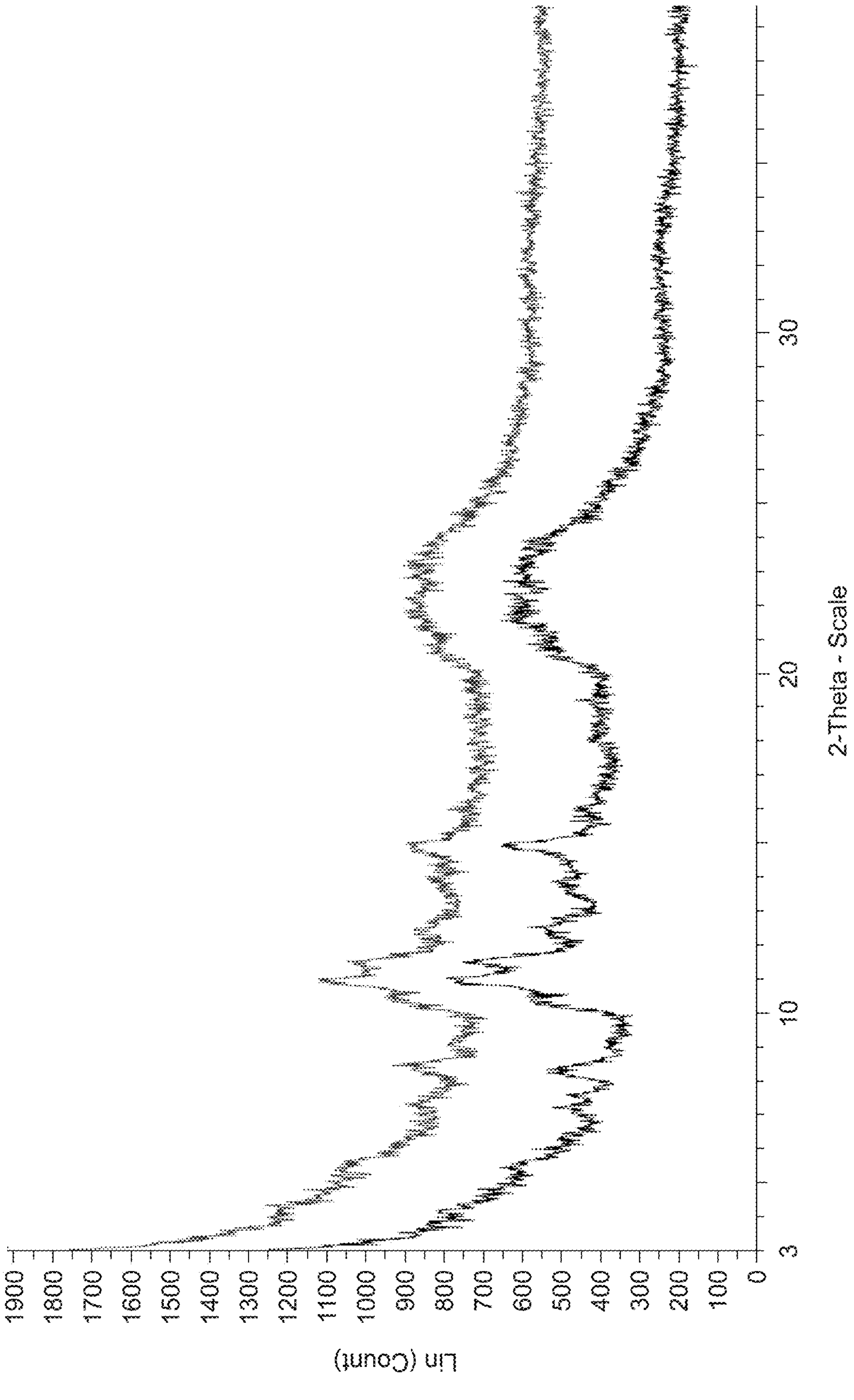
Figure 5B:
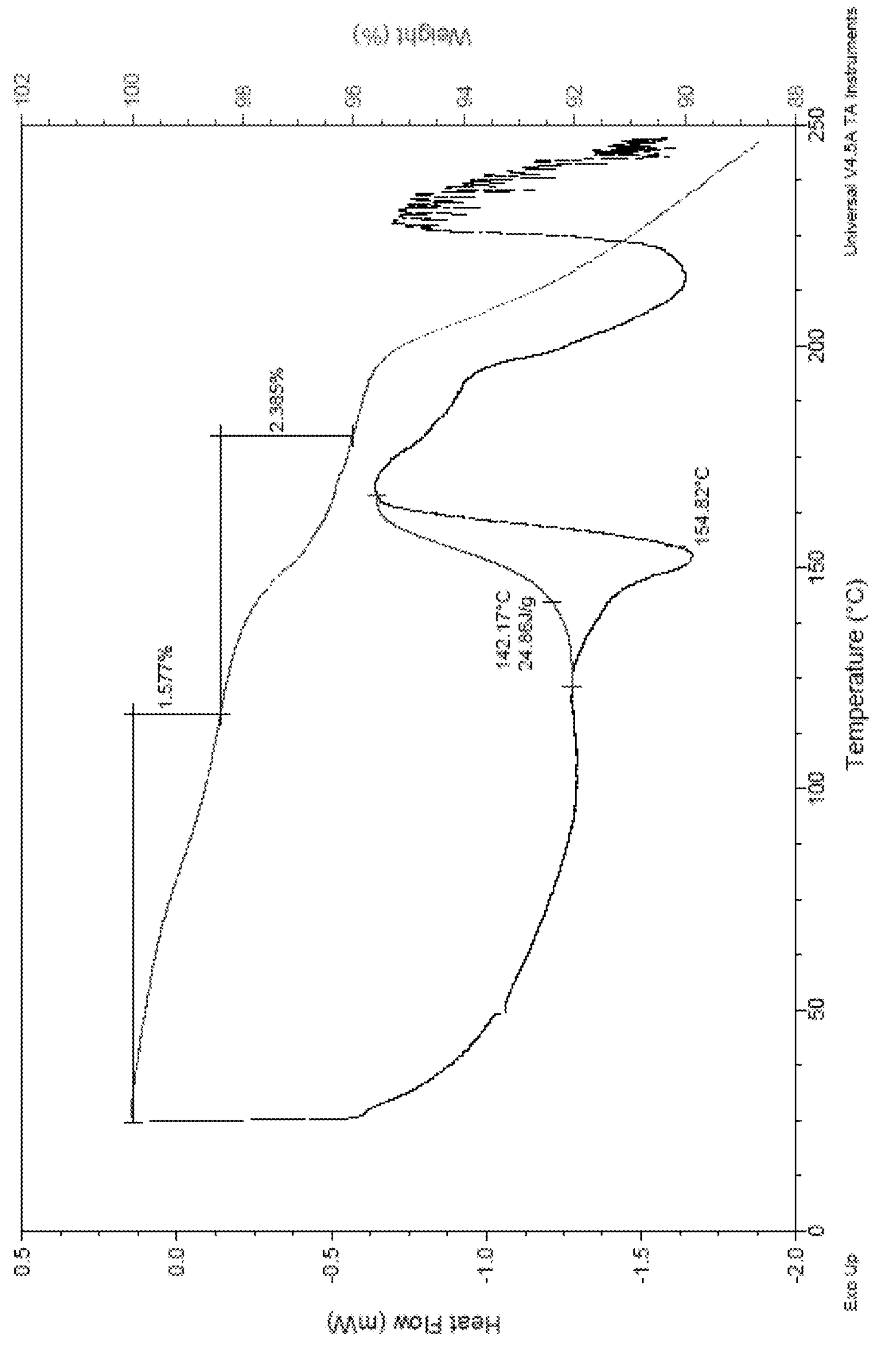

FIG. 5A shows representative XRPD spectra of a solid form of the free acid Compound FA, before (lower trace) and after (top trace) Dynamic moisture sorption analysis (DVS) studies. FIG. 5A shows that the solid form of the free acid did not change before and after the DVS studies, as evidenced by their XRPD spectra. FIG. 5B shows a representative DSC spectrum of the solid form of the free acid, Compound FA.

Figure 6A:
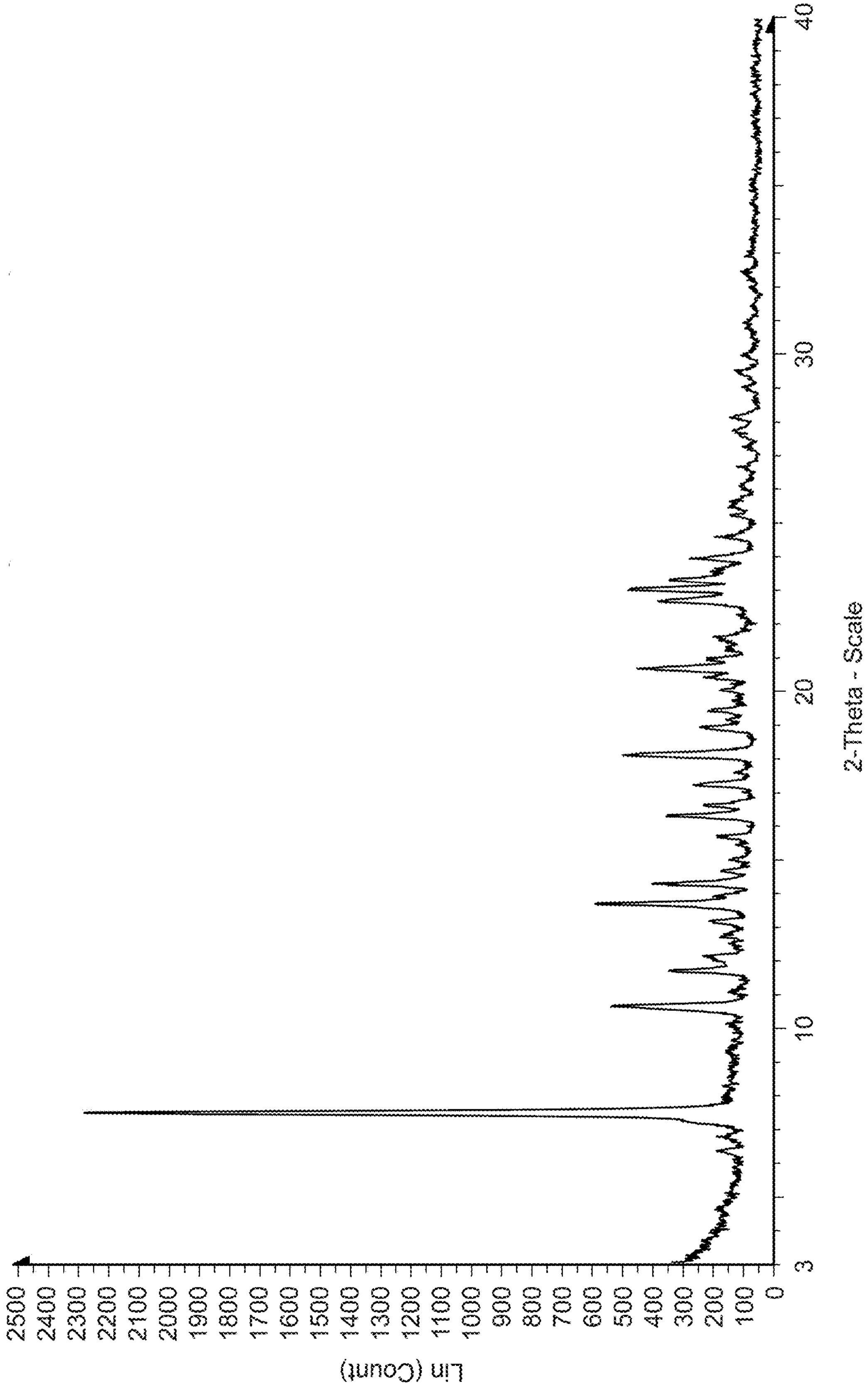
Figure 6B:
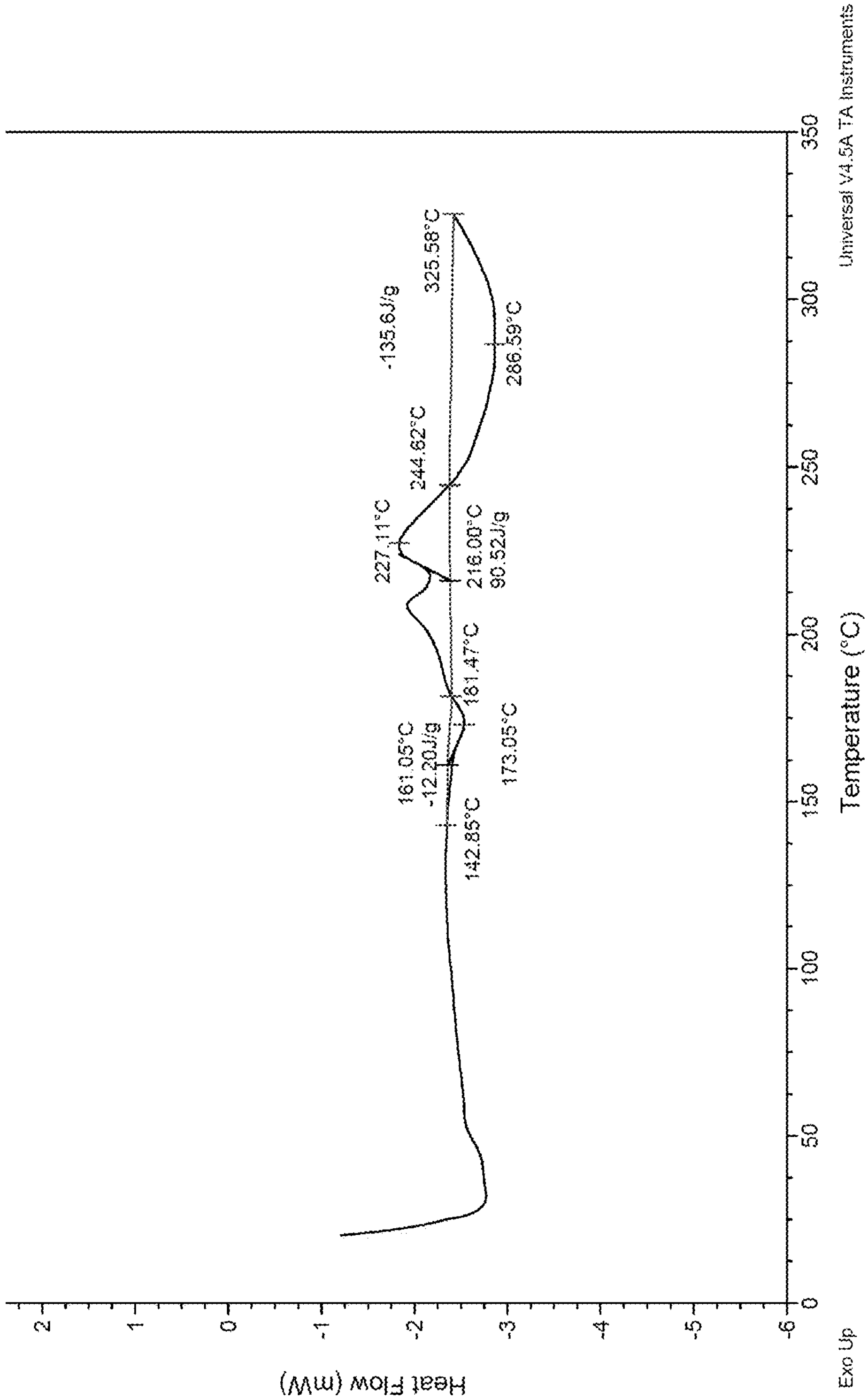

FIG. 6A shows a representative XRPD spectrum of a crystalline form of the diisopropylethyl amine salt of Compound FA (1:1 molar ratio) prepared in Example 2. FIG. 6B shows a representative DSC analysis of the crystalline form.

DETAILED DESCRIPTION

In various embodiments, the present disclosure is directed to novel salts of SERDs and pharmaceutical compositions comprising the salts. PCT/CN2018/123031, filed Dec. 24, 2018, and U.S. application Ser. No. 16/796,448, filed Feb. 20, 2020, the content of each of which is herein incorporated by reference in its entirety, describe that Compound FA, (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid, can form salts with some bases, such as alkali or alkaline bases, and amine bases, but not with a variety of acids that were tested, such as HCl. Some of the salts, such as the amine salts, can also exist in a solid form, which can be a crystalline, solvate, hydrate, or amorphous form. These salts offer alternative ways for preparing, formulating, and using Compound FA. As exemplified in the Examples section, some representative salt forms with L-lysine and meglumine of Compound FA can exist in various crystalline forms, which can have enhanced solubility in water at both pH 1.2 and 6.8 and can have enhanced stability compared to Compound FA itself (i.e., the free acid form).

In some embodiments, the salt forms herein can be more suited for various pharmaceutical uses compared to the free acid form.

The present disclosure further provides various pharmaceutical compositions, in particular, oral formulations (e.g., tablets or capsules) comprising Compound FA and salts thereof, such as the amine salts described herein. In some specific embodiments, the present disclosure provides pharmaceutical compositions comprising a meglumine salt of Compound FA, more specifically, tablets comprising meglumine salt of Compound FA, granules comprising meglumine salt of Compound FA, as well as methods of preparation and methods of using the same.

Amine Salts

In various embodiments, the present disclosure is directed to an amine salt (e.g., pharmaceutically acceptable amine salt) of (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid ("Compound FA"):

Compound FA

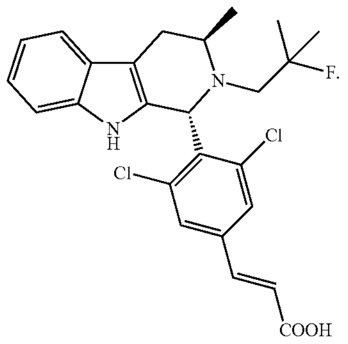

Compound FA can be referred to herein as in its free acid form to distinguish it from a salt formed with an external acid or base, even though internal ionization of the carboxylic acid function in Compound FA is theoretically possible.

Various amine salts are useful for the present disclosure. In some embodiments, the amine salt can be a meglumine salt, trialkyl amine salt, lysine salt, arginine salt, tromethamine salt, choline salt, or ammonium salt. Typically, the amine salt herein can exist in a solid form, such as in a crystalline form or an amorphous form, or a mixture thereof.

In some embodiments, the amine salt can be substantially pure. For example, in some embodiments, the amine salt of Compound FA (e.g., L-lysine salt or meglumine salt) is characterized by a purity by weight and/or by HPLC area of least 70% (e.g., at least 75%, at least 80%, at least 85%, at least 90%, at least 95%, at least 97%, or at least 99%). In some embodiments, the amine salt of Compound FA (e.g., L-lysine salt or meglumine salt) is characterized by a purity by weight and/or by HPLC area of about 70%, about 75%, about 80%, about 85%, about 90%, about 95%, about 97%, about 99%, or any ranges between the specified values. Unless otherwise obvious from context, for the purpose of calculating the weight percentage of the salt in the substantially pure salt, anything other than the salt, or a solvate or hydrate form thereof, is regarded as an impurity, which includes for example residual solvents, moisture contents, etc. For the avoidance of doubt, a composition comprising the substantially pure salt herein and one or more other ingredients should be understood as a mixture of the substantially pure salt herein and the one or more other ingredients, for example, such composition can be obtained directly or indirectly from mixing the substantially pure salt herein with the one or more other ingredients, such as water, pharmaceutically acceptable excipients, etc.

In some embodiments, the present disclosure provides a meglumine salt of Compound FA. Unless otherwise indicated to the contrary, the meglumine salt herein refers to a salt of Compound FA and meglumine in a 1:1 molar ratio. In any of the embodiments herein, the meglumine salt of Compound FA can be represented by the formula below:

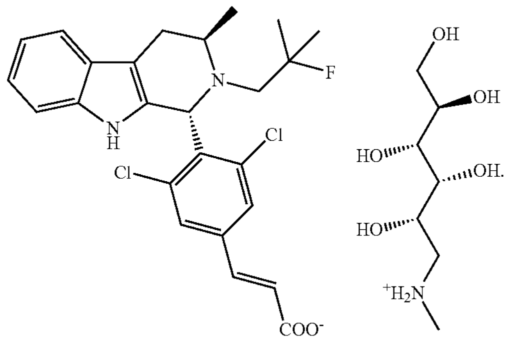

The meglumine salt of Compound FA can exist in various crystalline forms. In some embodiments, the meglumine salt can exist in Form I. In some embodiments, the meglumine salt can exist in Form II. In some embodiments, the meglumine salt can exist in Form III, which is determined to be a dihydrate form. As used herein, when a salt is said to exist or be in one particular crystalline form, it should be understood that in some embodiments, the salt can exist substantially in that particular form. However, in some embodiments, the salt can also exist in the particular form, in a mixture with one or more other solid forms, including amorphous form. For example, in some embodiments, the meglumine salt can exist substantially in Form I, such as more than 80% by weight, more than 90% by weight, or more than 95% by weight, and in some embodiments, no other solid form can be identified, for example, by XRPD. In some embodiments, the meglumine salt can exist in Form I, in a mixture with one or more solid forms selected from Form II, III, and amorphous form.

Some embodiments of the present disclosure are directed to Form I of the meglumine salt of Compound FA. As detailed in the Examples section, although Compound FA can exist in a solid form, the solid form is characterized as having low crystallinity. Compared to Compound FA itself, Form I of the meglumine salt exhibited more desirable stability, solubility, and other physicochemical profile, some of which are exemplified in the Examples section. For example, Form I of the meglumine salt has higher aqueous solubility at both pH 1.2 and 6.8 compared to Compound FA. Further, Form I was found to have good storage stability. For example, Form I remained unchanged after storage under the condition of 25° C./92.5% RH for 10 days. Also, as shown in details in the Examples section, crystalline Form I was successfully scaled up and thus can be manufactured in large scale. See, e.g., Example 2. Thus, Form I of the meglumine salt can be more suited for various pharmaceutical applications.

Figure 1A:
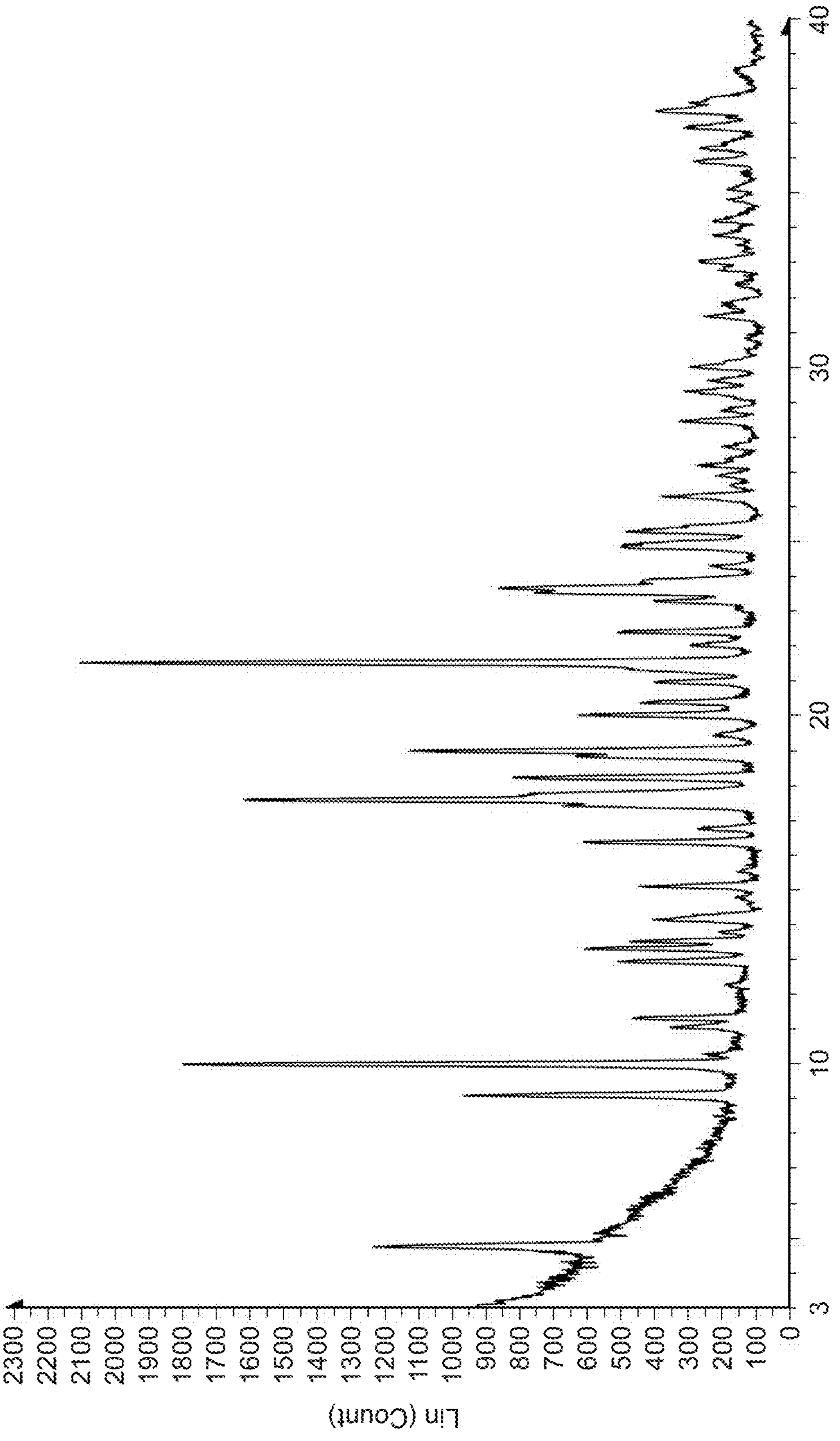
Figure 1B:
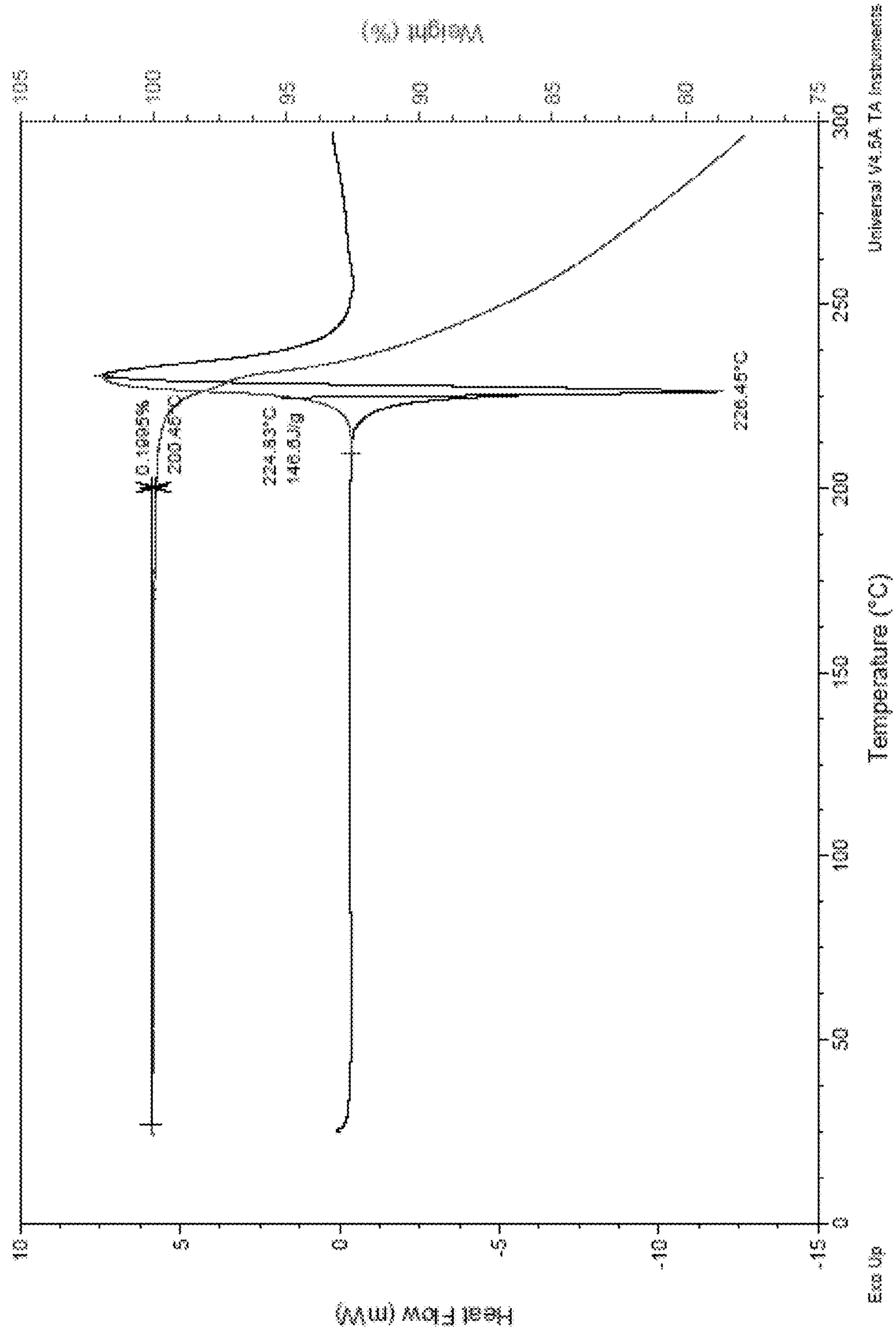

As used herein, Form I refers to a crystalline form of the meglumine salt of Compound FA, which can be characterized by (1) an XRPD pattern substantially the same as FIG. 1A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 1A, degrees 2 theta, ±0.2°; (3) an XRPD pattern having one or more (e.g., 1, 2, 3, 4, 5, 6, 7, or all) of the following peaks: 4.7, 9.1, 10.0, 17.6, 18.2, 19.0, 21.5, and 23.7 degrees 2 theta, ±0.2°; (4) an X-ray powder diffraction (XRPD) pattern having one or more (e.g., 8 or more, 12 or more, 16 or more, or 20 or more) of the following peaks: 4.7, 9.1, 10.0, 11.3, 13.0, 13.3, 13.5, 15.1, 16.4, 17.6, 18.2, 18.8, 19.0, 20.0, 20.4, 21.5, 22.4, 23.7, 23.9, 24.9, and 25.3 degrees 2 theta, ±0.2°; (5) a DSC pattern having an endotherm peak with an onset temperature of about 224.8° C. and/or peak temperature at about 226.5° C.; (6) a DSC profile substantially the same as shown in FIG. 1B; or any combination thereof (e.g., (1) and (5), (1) and (6), (2) and (5), (2) and (6), (3) and (5), (3) and (6), (4) and (5), or (4) and (6)). Major peaks of an XRPD spectrum as used herein refer to peaks having diffraction angles between 4-30 degrees (2 theta) and a relative intensity of 10% or above. In some embodiments, major peaks of an XRPD spectrum can refer to peaks with a relative intensity of 20% or above, 30% or above, 40% or above, 50% or above, 60% or above, 70% or above, 80% or above, or 90% or above. In some embodiments, the crystalline Form I can be characterized by an XRPD pattern having four or more (e.g., 4, 5, 6, 7, or all) of the following peaks: 4.7, 9.1, 10.0, 17.6, 18.2, 19.0, 21.5, and 23.7 degrees 2 theta, ±0.2°. In some embodiments, the crystalline Form I can be characterized by an XRPD pattern having all of the following peaks: 4.7, 9.1, 10.0, 17.6, 18.2, 19.0, 21.5, and 23.7 degrees 2 theta, ±0.2°.

Exemplary methods for preparing crystalline Form I of the meglumine salt are described herein. Typically, the method can include dissolving Compound FA in a solvent (e.g., methanol or isopropanol) to form a solution; adding about 1 equivalent of meglumine (e.g., in a methanol solution) to the solution to form the meglumine salt, which can be precipitated out. In some embodiments, Compound FA can also be suspended or partially dissolved in a solvent (e.g., methanol or isopropanol) to form a suspension or partial solution; and the method can include adding about 1 equivalent of meglumine (e.g., in a methanol solution) to the suspension or partial solution to form the meglumine salt, which can be precipitated out. Examples of preparations of Form I are provided herein. In some embodiments, Form I can also be prepared from other crystalline forms of meglumine salts. As shown in Example 3D, when stirred at room temperature in isopropanol, the mixture of solids with Form I, II, and dihydrate (Form III) can be converted into crystalline Form I as a final predominant solid form. Similarly, a mixture of Form I and dihydrate form III, when heated at 60° C. in water, can also be converted into Form I as a final predominant solid form.

In some embodiments, Form I can be recrystallized under suitable conditions with various solvents or combinations. Suitable solvents for recrystallization include, but are not limited to, THF, toluene, MeOH, ethanol, n-propanol, isopropanol, isobutanol, methyl tert-butyl ether, ether, isoamylol, butyl acetate, ethyl formate, 1,4-dioxane, n-butanol, tert-butanol, n-heptane, cyclohexane, methyl isobutyl ketone, dimethylbenzene, isobutyl acetate, 2-butanone, acetonitrile, acetone, ethyl acetate, isopropyl acetate, and water. The solvents can be used alone or in various combinations. Recrystallization technics are generally known in the art. For example, the meglumine salt of Compound FA can be slurried in one or more of the solvents at room temperature or under heat; the meglumine salt of Compound FA can be heated in one or more of the solvents followed by cooling; the meglumine salt of Compound FA can be dissolved in a solvent and then an antisolvent is added; and other techniques such as solid/liquid diffusion or liquid/liquid diffusion can also be used.

Figure 2A:
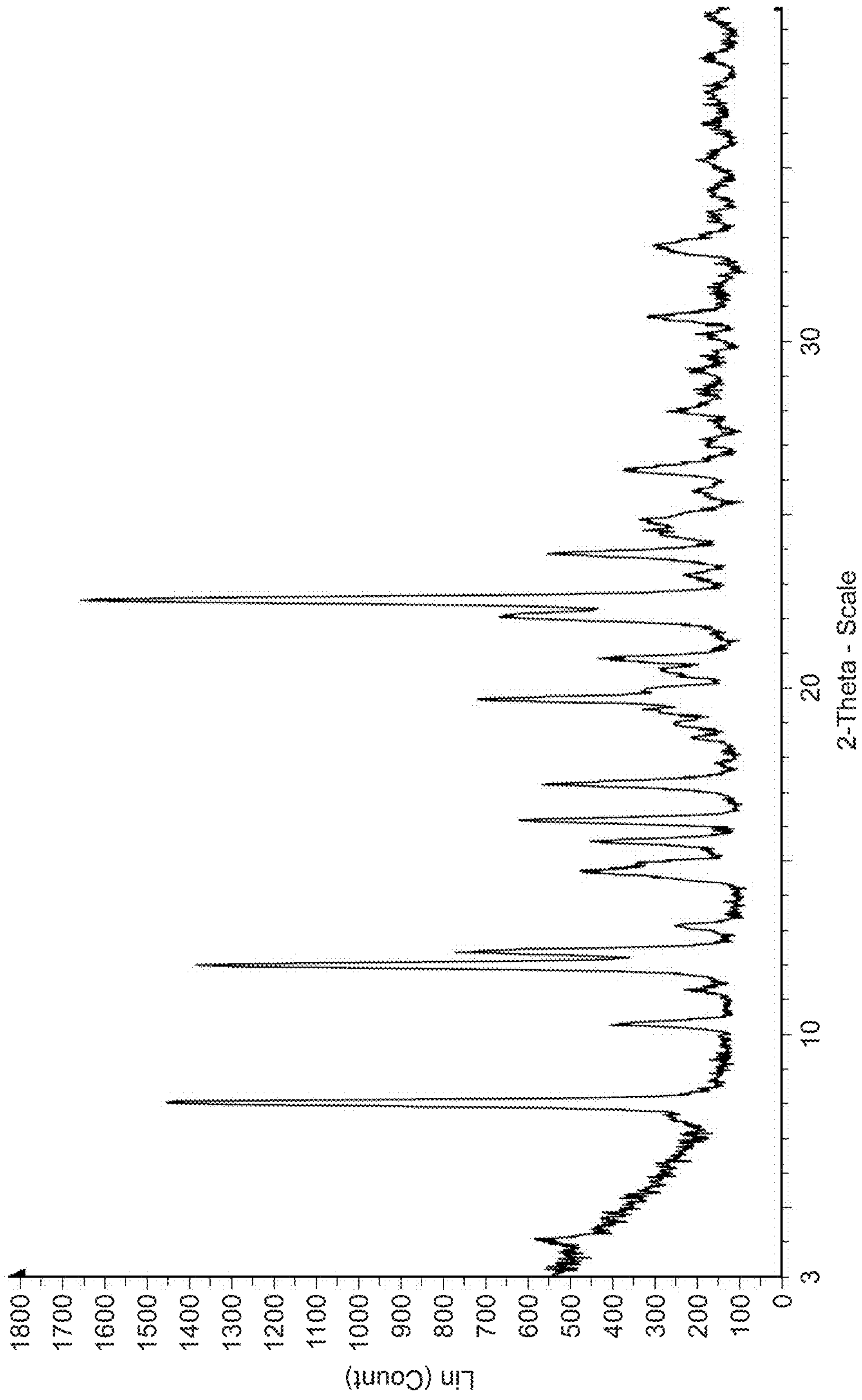
FIG. 2A shows a representative XRPD spectrum of crystalline form II of the meglumine salt of Compound FA.
Figure 2B:
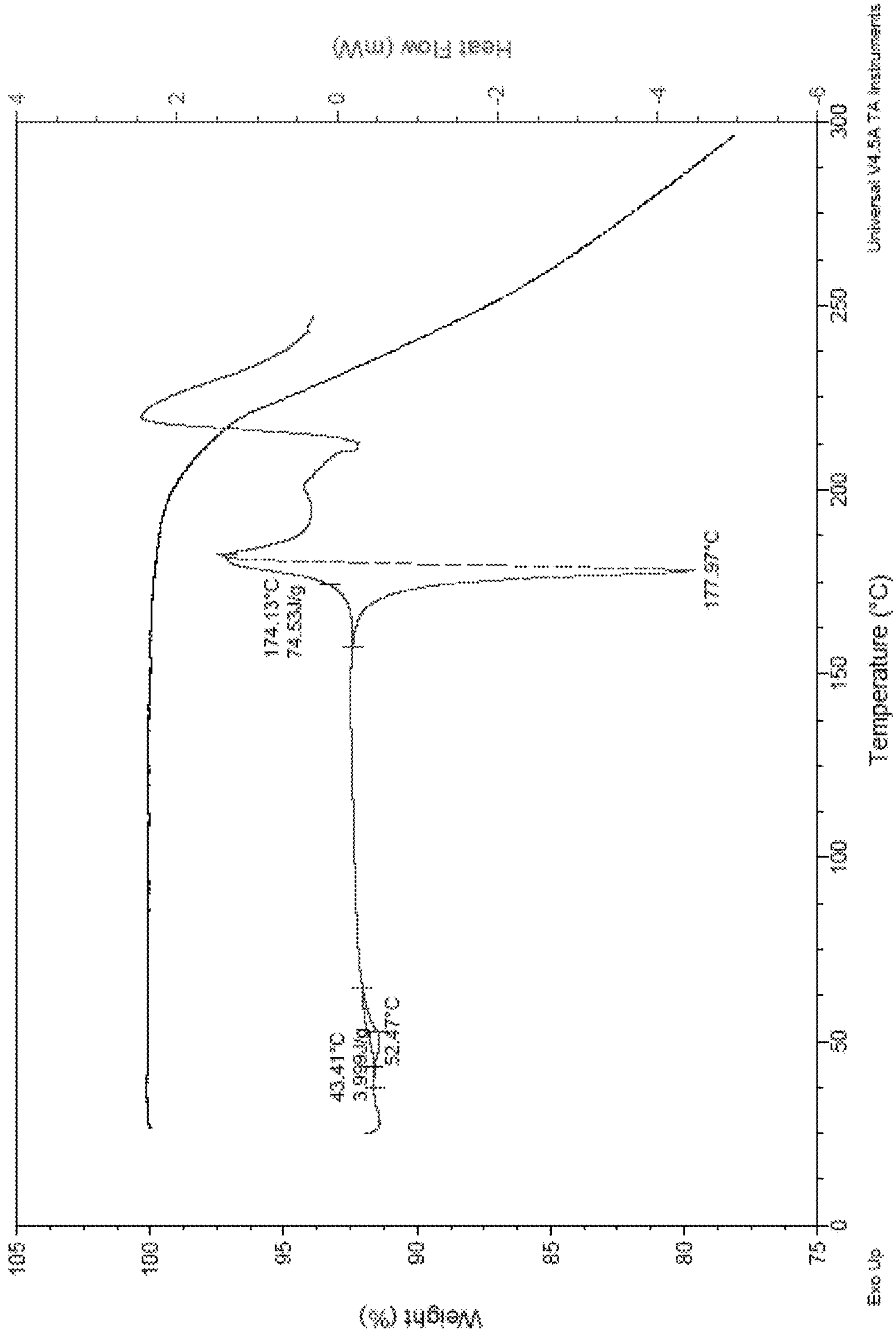
FIG. 2B shows a representative TGA and DSC analysis of crystalline form II of the meglumine salt of Compound FA.

Some embodiments of the present disclosure are directed to Form II of the meglumine salt of Compound FA. Form II can be prepared, for example, by drying the dihydrate form (Form III) of the meglumine salt of Compound FA. As used herein, Form II refers to a crystalline form of the meglumine salt of Compound FA, which can be characterized by (1) an XRPD pattern substantially the same as FIG. 2A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 2A, degrees 2 theta, ±0.2°; (3) an X-ray powder diffraction (XRPD) pattern having one or more (e.g., 1, 2, 3, 4, 5, 6, 7, 8, or 9) of the following peaks: 8.0, 12.0, 12.4, 16.1, 17.2, 19.7, 22.1, 22.5, and 23.9 degrees 2 theta, ±0.2°; (4) an X-ray powder diffraction (XRPD) pattern having one or more (e.g., 8 or more, 12 or more, or 16 or more) of the following peaks: 4.0, 8.0, 10.3, 12.0, 12.4, 14.7, 14.9, 15.5, 16.1, 17.2, 19.7, 20.8, 22.1, 22.5, 23.9, 24.5, 24.8, and 26.3 degrees 2 theta, ±0.2°; (5) a DSC pattern having an endotherm peak with an onset temperature of about 174.1° C. and/or a peak temperature at about 178.0° C.; (6) a DSC profile substantially the same as shown in FIG. 2B; or a combination thereof (e.g., (1) and (5), (1) and (6), (2) and (5), (2) and (6), (3) and (5), (3) and (6), (4) and (5), or (4) and (6)). For example, in some embodiments, the crystalline form II is characterized by an XRPD spectrum having four or more of the following peaks: 8.0, 12.0, 12.4, 16.1, 17.2, 19.7, 22.1, 22.5, and 23.9 degrees 2 theta, ±0.2°. In some embodiments, the crystalline form II is characterized by an XRPD spectrum having all of the following peaks: 8.0, 12.0, 12.4, 16.1, 17.2, 19.7, 22.1, 22.5, and 23.9 degrees 2 theta, ±0.2°.

Figure 3A:
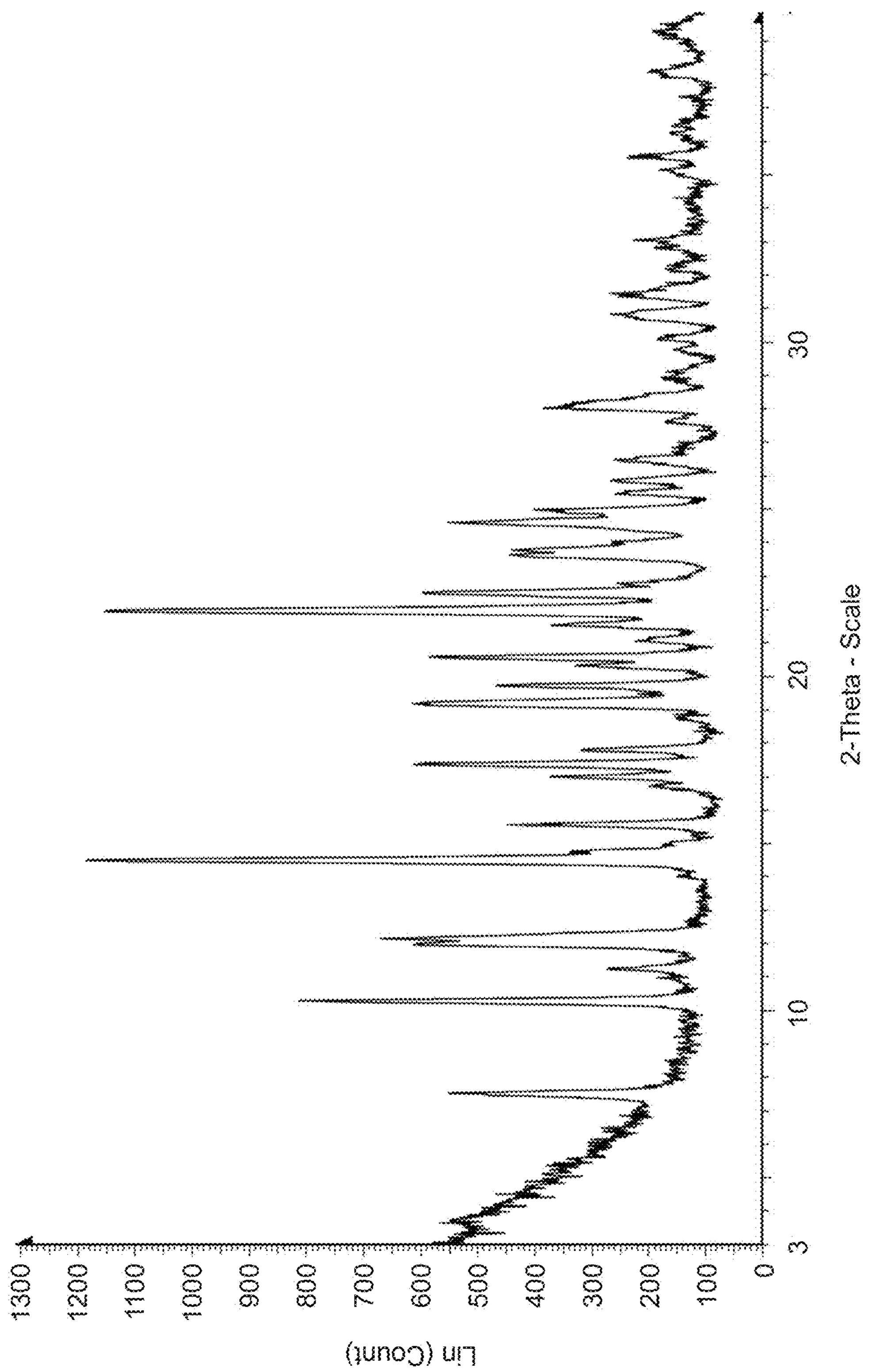
FIG. 3A shows a representative XRPD spectrum of crystalline form III (dihydrate) of the meglumine salt of Compound FA.
Figure 3B:
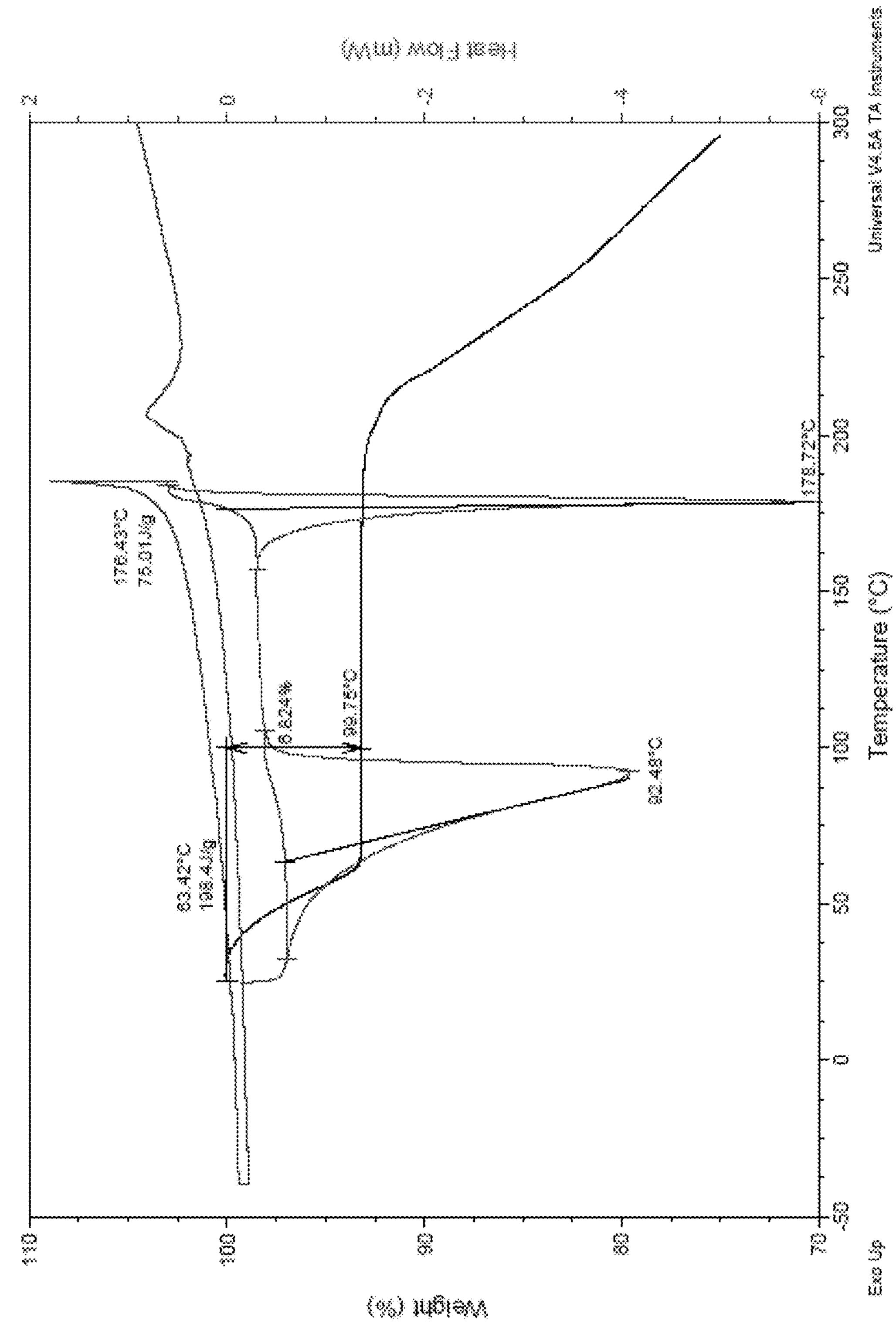
FIG. 3B shows a representative TGA and DSC analysis of crystalline form III of the meglumine salt of Compound FA.

The meglumine salt Form III is determined to be a hydrate form, more particularly, a dihydrate form. The dihydrate form III can be a stable solid form. For example, as shown in the interconversion experiment, stirring a mixture of Form I, II, and III in water at room temperature can result into the dihydrate form III as a final predominant solid form. Exemplary methods for preparing the dihydrate form are described in the Examples section. As used herein, Form III refers to a crystalline form of the meglumine salt of Compound FA, which can be characterized by (1) an XRPD pattern substantially the same as FIG. 3A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 3A, degrees 2 theta, ±0.2°; (3) an X-ray powder diffraction (XRPD) pattern having one or more (e.g., 1, 2, 3, 4, 5, 6, 7, 8, 9, 10, 11, 12, 13, 14, 15, 16, or 17) of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°; (4) an X-ray powder diffraction (XRPD) pattern having one or more (e.g., 8 or more, 12 or more, 16 or more, 20 or more, or 24 or more) of the following peaks: 3.7, 6.4, 7.5, 10.2, 11.2, 12.0, 14.5, 15.6, 17.0, 17.4, 17.8, 19.2, 19.7, 20.3, 20.6, 21.5, 22.0, 22.5, 22.8, 23.8, 24.6, 24.9, 25.5, 25.9, 26.5, 28.1, 30.9, and 31.4 degrees 2 theta, ±0.2°; (5) a DSC pattern having two endotherm peaks with onset temperatures of about 63.4° C. and 176.4° C. and/or respective peak temperatures at about 92.5° C. and 178.7° C.; (6) a DSC profile substantially the same as shown in FIG. 3B; or a combination thereof (e.g., (1) and (5), (1) and (6), (2) and (5), (2) and (6), (3) and (5), (3) and (6), (4) and (5), or (4) and (6)). For example, in some embodiments, the crystalline form III is characterized by an XRPD spectrum having four or more of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°. In some embodiments, the crystalline form III is characterized by an XRPD spectrum having eight or more of the following peaks: 7.5, 10.2, 12.0, 15.6, 17.0, 17.4, 19.2, 19.7, 20.6, 21.5, 22.0, 22.5, 23.8, 24.9, and 28.1 degrees 2 theta, ±0.2°. In some embodiments, the crystalline form III is characterized by an XRPD spectrum having twelve or more of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°. In some embodiments, the crystalline form III is characterized by an XRPD spectrum having all of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°.

In some embodiments, the present disclosure also provides a meglumine salt produced by any of the following Procures 1-4.

Procedure 1: 23.45 mg of Compound FA was dissolved in 500 μL of 0.1 M meglumine/(methanol-water) solution. The clear solution was kept stirring for an hour. Concentrated and precipitation occurred. Add 200 μL of isopropyl acetate, and the solution became clear. Stirred for about 10 min, solid appeared. Added another 600 μL of isopropyl acetate, and kept stirring for 20 min. The solid sample was collected by filtration. The sample was dry under vacuum overnight at 40° C.

Procedure 2: 24.02 mg of Compound FA was dissolved in 1 mL of 0.05 M meglumine/water solution. The clear solution was kept stirring at room temperature for an hour. Concentrated to about 50 μL, add 400 μL of isopropyl acetate. Stirred for about 10 min, solid appeared. Added another 200 μL of isopropyl acetate, and kept stirring for an hour. The solid sample was collected by filtration.

Procedure 3: 24.01 mg of Compound FA was dissolved in 500 μL of 0.1 M meglumine/(methanol-water) solution. The clear solution was kept stirring at room temperature for an hour. Concentrated to solid sample appeared, and added 400 μL of water. Stirred for 30 min, the product was obtained by filtration. Dry under vacuum overnight at 40° C., the sample was characterized.

Procedure 4: 23.13 mg of Compound FA was dissolved in 500 μL of IPA (isopropanol) with stirring at room temperature. Added 1 mL of 0.05 M meglumine/methanol solution. The clear solution was kept stirring at room temperature for an hour. Concentrated to solid sample appeared, and added 200 μL of IPA. Stirred for 30 min at room temperature, the product was obtained by filtration.

Figure 4A:
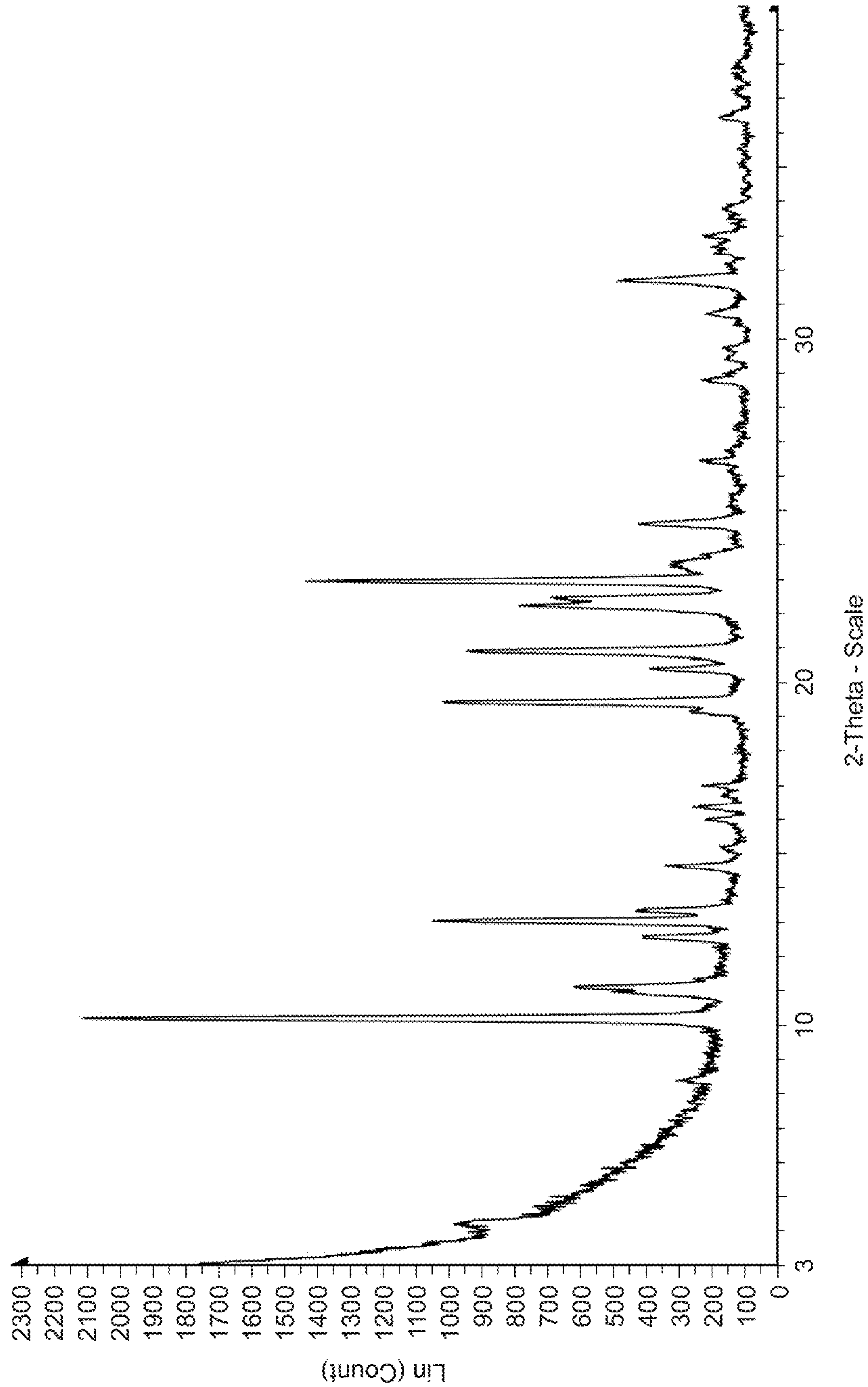
FIG. 4A shows a representative XRPD spectrum of crystalline form A of the L-lysine salt of Compound FA (1:1 molar ratio).
Figure 4B:
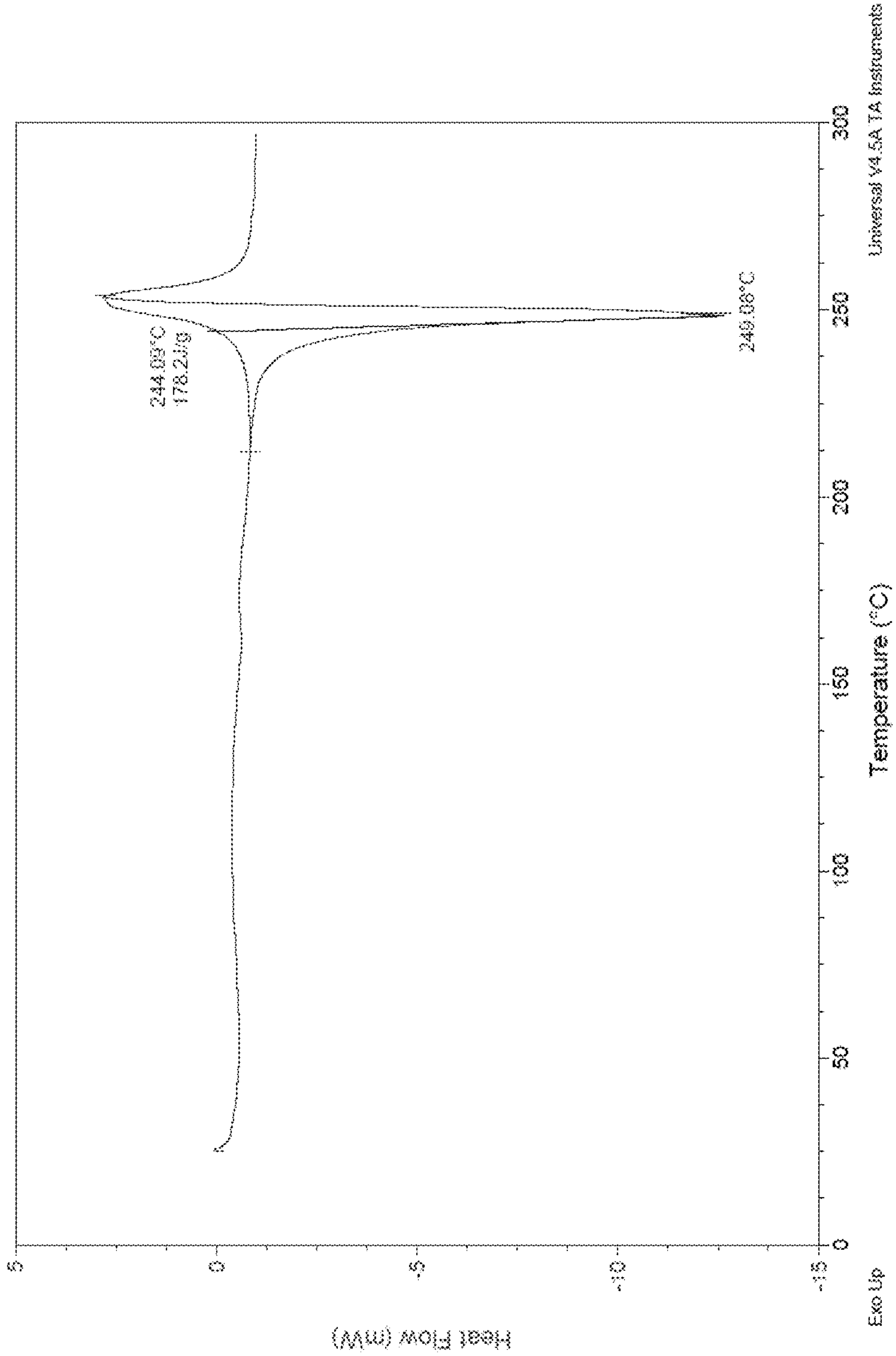
FIG. 4B shows a representative DSC analysis of the crystalline form A.

In some embodiments, the present disclosure also provides a lysine salt of Compound FA. In some embodiments, the lysine salt is an L-lysine salt with the molar ratio of lysine to Compound FA at about 1:1. In some embodiments, the L-lysine salt of Compound FA is in a crystalline form or an amorphous form, or a mixture thereof. In some embodiments, the L-lysine salt is in a crystalline Form A. Crystalline Form A as used herein refers to a crystalline form of the L-lysine salt of Compound FA (1:1 molar ratio), which can be characterized by (1) an XRPD pattern substantially the same as FIG. 4A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 4A, degrees 2 theta, ±0.2°; (3) an X-ray powder diffraction (XRPD) pattern having one or more (e.g., 1, 2, 3, 4, 5, 6, or 7) of the following peaks: 10.2, 13.0, 19.4, 20.9, 22.2, 22.4, and 22.9 degrees 2 theta, ±0.2°; (4) an X-ray powder diffraction (XRPD) pattern having one or more (e.g., 4 or more, 8 or more, 10 or more, or all) of the following peaks: 4.2, 10.2, 11.1, 13.0, 13.3, 19.4, 20.9, 22.2, 22.4, 22.9, 24.6, and 31.7 degrees 2 theta, ±0.2°; (5) a DSC pattern having an endotherm peak with an onset temperature of about 244.1° C. and/or a peak temperature at about 249.1° C.; (6) a DSC profile substantially the same as shown in FIG. 4B; or a combination thereof (e.g., (1) and (5), (1) and (6), (2) and (5), (2) and (6), (3) and (5), (3) and (6), (4) and (5), or (4) and (6)). In some embodiments, the crystalline form A is characterized by an XRPD spectrum having four or more of the following peaks: 10.2, 13.0, 19.4, 20.9, 22.2, 22.4, and 22.9 degrees 2 theta, ±0.2°. In some embodiments, the crystalline form A is characterized by an XRPD spectrum having all the following peaks: 10.2, 13.0, 19.4, 20.9, 22.2, 22.4, and 22.9 degrees 2 theta, ±0.2°.

In some embodiments, the present disclosure also provides a lysine salt produced by any of the following Procures A-C.

Procedure A: 23.93 mg of Compound FA was dissolved in 400 μL of isobutanol with stirring at 50° C. Added 25 μL 1 M of L-lysine/water solution (0.5 eq.) and reacted at 50° C. Precipitation occurred in about 5 minutes. Reacted for another 20 min, the reaction solution was cooled slowly to room temperature. The sample was collected by filtration.

Procedure B: 24.00 mg of Compound FA was dissolved in 400 μL of isobutanol with stirring at 50° C. Added 50 μL 1 M of L-lysine/water solution (1 eq.) and reacted at 50° C. Precipitation occurred about 13 min later. Reacted for other 15 min, the reaction solution was cooled slowly to room temperature. The sample was collected by filtration.

Procedure C: 14.82 mg of lysine was added in 478 μL of methanol. After stirring for 30 min at room temperature, solid sample could not dissolve. Added 43.88 mg of Compound FA, the solution was still cloudy. Kept stirring at room temperature overnight, the solid sample was obtained by filtration.

Some embodiments of the present disclosure are also directed to other amine salts. For example, in some embodiments, a trialkylamine salt of Compound FA is provided. Such trialkylamine salt can be used in a pharmaceutical composition directly or can be used to facilitate the manufacturing of Compound FA or its salts. See e.g., Example 2. In some embodiments, the trialkylamine salt is a diisopropylethyl amine salt. In some embodiments, the trialkyl amine salt is a diisopropylethyl amine salt of Compound FA represented by the structure below:

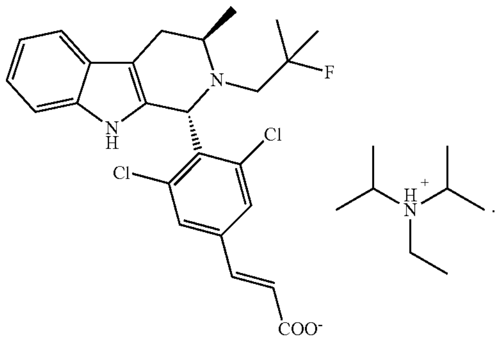

In some embodiments, the diisopropylethyl amine salt is in a crystalline form. In some embodiments, the diisopropylethyl amine salt can be in a solid form characterized by (1) an XRPD pattern substantially the same as shown in FIG. 6A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 6A, degrees 2 theta, ±0.2°; (3) a DSC profile substantially the same as shown in FIG. 6B; or a combination thereof.

Pharmaceutical Compositions

In various embodiments, the present disclosure also provides pharmaceutical compositions comprising a salt of the present disclosure, such as an amine salt described herein, and optionally a pharmaceutically acceptable excipient. In certain embodiments, a pharmaceutical composition described herein comprises a salt of the present disclosure, such as an amine salt described herein, and a pharmaceutically acceptable excipient. The pharmaceutical compositions described herein are useful in treating and/or preventing proliferative diseases (e.g., ER+ breast cancer) or diseases associated with ER.

In some embodiments, the present disclosure provides a pharmaceutical composition comprising one or more of the salts of the present disclosure (e.g., the amine salts of Compound FA, such as Form I, II, or III of meglumine salt of Compound FA or Form A of the lysine salt of Compound FA). Typically, the pharmaceutical composition comprises a therapeutically effective amount of one or more of the salts of the present disclosure (e.g., Form I, II, or III of meglumine salt of Compound FA or Form A of the lysine salt of Compound FA) and optionally a pharmaceutically acceptable excipient or carrier. In some embodiments, the pharmaceutical composition comprises about 1 mg to about 2,000 mg (e.g., about 10 mg, about 50 mg, about 100 mg, about 200 mg, about 300 mg, about 500 mg, about 800 mg, about 1000 mg, about 1500 mg, about 2000 mg, or any ranges between the recited values such as about 10-1000 mg, about 50-500 mg, etc.) of one or more of the salts of the present disclosure (e.g., Form I, II, or III of meglumine salt of Compound FA or Form A of the lysine salt of Compound FA) and optionally a pharmaceutically acceptable excipient or carrier. In some embodiments, the pharmaceutical composition comprises one or more of the substantially pure amine salts as described herein, e.g., in the amount described herein. In some embodiments, the pharmaceutical composition comprises one or more of the crystalline forms selected from Form I, II, III of meglumine salt of Compound FA and Form A of the lysine salt of Compound FA.

In some specific embodiments, the pharmaceutical composition comprises Form I of the meglumine salt of Compound FA. In some specific embodiments, the active ingredient in the pharmaceutical composition can comprise, consist essentially of, or consist of the meglumine salt of Compound FA in Form I. In some embodiments, Compound FA exists in the pharmaceutical composition essentially in Form I, for example, at least 80% (e.g., at least 85%, at least 90%, at least 95%, by weight of total Compound FA) of Compound FA exist in the pharmaceutical composition in Form I. In some embodiments, the pharmaceutical composition is substantially free of Compound FA in any other solid form, such as other salts or other crystalline forms. For example, in some embodiments, the pharmaceutical composition is free or substantially free of Compound FA in its free acid form, for example, the pharmaceutical composition can in some embodiments include less than 10%, less than 5%, less than 2%, less than 1%, by weight of total Compound FA, or non-detectable amount, of Compound FA in its free acid form. In some embodiments, the pharmaceutical composition is free or substantially free of Compound FA in a salt form other than meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a salt form other than meglumine salt of Compound FA (1:1 molar ratio). In some embodiments, the pharmaceutical composition is free or substantially free of Compound FA in a crystalline form other than Form I of the meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a crystalline form other than Form I. Weight of total Compound FA in a pharmaceutical composition, as used herein, refers to the weight of all forms of Compound FA combined, including for example, free acid form, salts, crystalline forms, amorphous forms, hydrates, solvates etc., expressed in equivalent weight of Compound FA as a free acid. For the calculation of the weight percentages of each different form in a given pharmaceutical composition, it should be clear to those skilled in the art that the weight of each different form will be first converted into its respective equivalent weight of Compound FA as a free acid, which is then divided by the weight of total Compound FA as defined herein.

In some specific embodiments, the active ingredient in the pharmaceutical composition can comprise, consist essentially of, or consist of the meglumine salt of Compound FA in Form I, amorphous form, or a mixture thereof. In some embodiments, Compound FA can exist in the pharmaceutical composition as a mixture of Form I and an amorphous form of the meglumine salt of Compound FA, for example, at least 80% (e.g., at least 85%, at least 90%, at least 95%, by weight of total Compound FA) of Compound FA can exist in the pharmaceutical composition in Form I or an amorphous form.

In some specific embodiments, the pharmaceutical composition comprises Form II of the meglumine salt of Compound FA. In some specific embodiments, the active ingredient in the pharmaceutical composition can comprise, consist essentially of, or consist of the meglumine salt of Compound FA in Form II. In some embodiments, Compound FA exists in the pharmaceutical composition essentially in Form II, for example, at least 80% (e.g., at least 85%, at least 90%, at least 95%, by weight of total Compound FA) of Compound FA exist in the pharmaceutical composition in Form II. In some embodiments, the pharmaceutical composition is substantially free of Compound FA in any other solid forms, such as other salts or other crystalline form. For example, in some embodiments, the pharmaceutical composition is free or substantially free of Compound FA in its free acid form, for example, the pharmaceutical composition can in some embodiments include less than 10%, less than 5%, less than 2%, less than 1%, by weight of total Compound FA, or non-detectable amount, of Compound FA in its free acid form. In some embodiments, the pharmaceutical composition is free or substantially free of Compound FA in a salt form other than meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a salt form other than meglumine salt of Compound FA (1:1 molar ratio). In some embodiments, the pharmaceutical composition is free or substantially free of Compound FA in a crystalline form other than Form II of the meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a crystalline form other than Form II. In some specific embodiments, the active ingredient in the pharmaceutical composition can comprise, consist essentially of, or consist of the meglumine salt of Compound FA in Form II, amorphous form, or a mixture thereof. In some embodiments, Compound FA can exist in the pharmaceutical composition as a mixture of Form II and an amorphous form of the meglumine salt of Compound FA, for example, at least 80% (e.g., at least 85%, at least 90%, at least 95%, by weight of total Compound FA) of Compound FA can exist in the pharmaceutical composition in Form II or an amorphous form.

In some specific embodiments, the pharmaceutical composition comprises Form III of the meglumine salt of Compound FA. In some specific embodiments, the active ingredient in the pharmaceutical composition can comprise, consist essentially of, or consist of the meglumine salt of Compound FA in Form III. In some embodiments, Compound FA exists in the pharmaceutical composition essentially in Form III, for example, at least 80% (e.g., at least 85%, at least 90%, at least 95%, by weight of total Compound FA) of Compound FA exist in the pharmaceutical composition in Form III. In some embodiments, the pharmaceutical composition is substantially free of Compound FA in any other solid forms, such as other salts or other crystalline form. For example, in some embodiments, the pharmaceutical composition is free or substantially free of Compound FA in its free acid form, for example, the pharmaceutical composition can in some embodiments include less than 10%, less than 5%, less than 2%, less than 1%, by weight of total Compound FA, or non-detectable amount, of Compound FA in its free acid form. In some embodiments, the pharmaceutical composition is free or substantially free of Compound FA in a salt form other than meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a salt form other than meglumine salt of Compound FA (1:1 molar ratio). In some embodiments, the pharmaceutical composition is free or substantially free of Compound FA in a crystalline form other than Form III of the meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a crystalline form other than Form III. In some specific embodiments, the active ingredient in the pharmaceutical composition can comprise, consist essentially of, or consist of the meglumine salt of Compound FA in Form III, amorphous form, or a mixture thereof. In some embodiments, Compound FA can exist in the pharmaceutical composition as a mixture of Form III and an amorphous form of the meglumine salt of Compound FA, for example, at least 80% (e.g., at least 85%, at least 90%, at least 95%, by weight of total Compound FA) of Compound FA can exist in the pharmaceutical composition in Form III or an amorphous form.

Typically, the pharmaceutical composition comprising the meglumine salt of Compound FA (e.g., in Form I, II, III, and/or amorphous form) does not include a significant amount of Compound FA as a free acid. In some embodiments, the pharmaceutical composition described herein above can also include a mixture of the meglumine salt and the free acid form (other than and in addition to any amount that may exist through equilibrium).

Other salts, for example, any one or more of other amine salts of Compound FA described herein, such as the L-lysine salt of Compound FA (1:1 molar ratio), can be formulated similarly to those described herein for the meglumine salt of Compound FA, such as Form I.

For example, in some embodiments, the pharmaceutical composition can comprise Form A of the L-lysine salt of Compound FA. In some specific embodiments, the active ingredient in the pharmaceutical composition can comprise, consist essentially of, or consist of the L-lysine salt of Compound FA in Form A. In some embodiments, Compound FA exists in the pharmaceutical composition essentially in Form A, for example, at least 80% (e.g., at least 85%, at least 90%, at least 95%, by weight of total Compound FA) of Compound FA exist in the pharmaceutical composition in Form A. In some embodiments, the pharmaceutical composition is substantially free of Compound FA in any other solid form, such as other salts or other crystalline form. For example, in some embodiments, the pharmaceutical composition is free or substantially free of Compound FA in its free acid form, for example, the pharmaceutical composition can in some embodiments include less than 10%, less than 5%, less than 2%, less than 1%, by weight of total Compound FA, or non-detectable amount, of Compound FA in its free acid form. In some embodiments, the pharmaceutical composition is free or substantially free of Compound FA in a salt form other than L-lysine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a salt form other than L-lysine salt of Compound FA (1:1 molar ratio). In some embodiments, the pharmaceutical composition is free or substantially free of Compound FA in a crystalline form other than Form A of the L-lysine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a crystalline form other than Form A. However, in some embodiments, the pharmaceutical composition can also comprise amorphous form of the L-lysine salt of FA (1:1 molar ratio).

Others salts such as tromethamine salts, choline salts, etc. can be formulated similarly.

Typically, the salt of the present disclosure (e.g., the amine salts of Compound FA, such as Form I, II, or III of meglumine salt of Compound FA or Form A of the lysine salt of Compound FA) is provided in an effective amount in the pharmaceutical composition. In certain embodiments, the effective amount is a therapeutically effective amount (e.g., amount effective for treating a proliferative disease in a subject in need thereof). In certain embodiments, the proliferative disease is cancer, e.g., ER+ breast cancer. In certain embodiments, the effective amount is a prophylactically effective amount (e.g., amount effective for preventing a proliferative disease in a subject in need thereof and/or for keeping a subject in need thereof in remission of a proliferative disease).

Pharmaceutical compositions described herein can be prepared by any method known in the art of pharmacology. In general, such preparatory methods include bringing the active ingredient, such as the salt of the present disclosure, into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients useful for the manufacture of the pharmaceutical compositions herein include, for example, inert diluents, dispersing and/or granulating agents, surface active agents such as surfactants and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

The pharmaceutical composition can be formulated for any routes of administration, for example, oral administration. Typically, the pharmaceutical composition is a solid dosage form. However, in some embodiments, other dosage forms such as liquid, suspension, syrup, or semi-solid dosage forms can also be used.

Solid dosage forms for oral administration include for example capsules, tablets, dispersible tablets, pellet, beads, pills, powders, and granules. In such solid dosage forms, the active ingredient is mixed with at least one inert, pharmaceutically acceptable excipient or carrier (a) fillers or extenders such as starch, lactose, sucrose, glucose, mannitol, calcium carbonate, calcium phosphate-dibasic, calcium phosphate-tribasic, calcium sulfate, microcrystalline cellulose, silicified microcrystalline cellulose, dextrates, dextrins, dextrose, sorbitol, pregelatinized starch or mixtures thereof, (b) binders such as, for example, carboxymethylcellulose, alginates, gelatin, polyvinylpyrrolidinone, sucrose, pregelatinized starch, hydroxypropylmethyl cellulose, hydroxy propyl cellulose, acacia, and combinations thereof (c) humectants such as glycerol, (d) disintegrating agents such as cross-linked polyvinylpyrrolidone, sodium starch glycolate, croscarmellose sodium, low-substituted hydroxypropyl cellulose, potato or tapioca starch, and combinations thereof, (f) absorption accelerators such as quaternary ammonium compounds, (g) wetting agents such as, cetyl alcohol and glycerol monostearate, (h) absorbents such as kaolin and bentonite clay, and (i) lubricants such as talc, calcium stearate, magnesium stearate, stearic acid, hydrogenated castor oil, sodium stearyl fumarate, solid polyethylene glycols, sodium lauryl sulfate, and mixtures thereof. In the case of capsules, tablets, and pills, the dosage form may include a buffering agent.

Solid compositions of a similar type can be employed as fillers in hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmaceutical science They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in hard-filled gelatin capsules using such excipients as lactose or milk sugar as well as high molecular weight polethylene glycols and the like.

The active ingredient (e.g., the salts of the present disclosure) can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The salts of the present disclosure are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or salt described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition herein or salt of the present disclosure. In some embodiments, the pharmaceutical composition or salt of the present disclosure provided in the first container and the second container are combined to form one unit dosage form.

In certain embodiments, a kit described herein includes a first container comprising a salt of the present disclosure or pharmaceutical composition described herein. In certain embodiments, a kit described herein is useful in treating a proliferative disease (e.g., ER+ breast cancer) in a subject in need thereof, and/or preventing a proliferative disease in a subject in need thereof. In some embodiments, the SERDs described herein are useful in treating diseases and/or disorders associated with a steroid hormone such as estrogen.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, and/or preventing a proliferative disease in a subject in need thereof. A kit described herein may include one or more additional pharmaceutical agents described herein as a separate composition. In some embodiments, the one or more additional agents can be one or more additional antiproliferative agents, which can be included with the salt herein in the same or a separate composition. In some embodiments, the antiproliferative agent can be a CDK4/CDK6 inhibitor, such as seliciclib, UCN-01, P1446A-05, palbociclib (PD-0332991), abemaciclib, dinaciclib, P27-00, AT-7519, RGB286638, and SCH727965, etc. In some embodiments, the antiproliferative agent can be a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In some embodiments, the antiproliferative agent can be one or more agents selected from EGFR inhibitors, MEK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs. Where desired, the salts and pharmaceutical compositions herein can also be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Exemplary Pharmaceutical Compositions and Methods of Preparation

In some embodiments, the present disclosure provides certain pharmaceutical compositions comprising Compound FA or a pharmaceutically acceptable salt thereof (e.g., those described herein). For example, in some embodiments, the pharmaceutical composition can comprise Compound FA or an amine salt of Compound FA (e.g., described herein). In some embodiments, the total Compound FA in the pharmaceutical composition, expressed as equivalent weight of the free acid Compound FA, can range from about 5 mg to about 1.2 grams (e.g., about 10 mg, about 50 mg, about 100 mg, about 200 mg, about 300 mg, about 500 mg, about 750 mg, about 800 mg, about 1000 mg, about 1200 mg, or any ranges between the recited values such as about 10-1000 mg, about 10-800 mg, about 10-500 mg, about 10-300 mg, about 50-800 mg, about 50-500 mg, etc.) of Compound FA. The pharmaceutical composition is typically an oral dosage form, such as a tablet, pill, capsule, granule, etc.

In some specific embodiments, the present disclosure provides a pharmaceutical composition comprising a meglumine salt of Compound FA. The pharmaceutical composition is typically an oral dosage form, such as a tablet, pill, capsule, granule, etc. In some embodiments, the pharmaceutical composition is a tablet or a capsule. In some embodiments, the pharmaceutical composition is a coated tablet, such as a non-enteric coated tablet. In some embodiments, the pharmaceutical composition is in a unit dosage form. For example, in some embodiments, a single tablet or capsule can comprise Compound FA or an amine salt of Compound FA (e.g., a meglumine salt as described herein) in the amount described herein, such as equivalent to about 5 mg to about 1.2 grams Compound FA.

The pharmaceutical composition typically comprises the meglumine salt of Compound FA in an amount equivalent to about 5 mg to about 1.2 grams (e.g., about 10 mg, about 50 mg, about 100 mg, about 200 mg, about 300 mg, about 500 mg, about 750 mg, about 800 mg, about 1000 mg, about 1200 mg, or any ranges between the recited values such as about 10-1000 mg, about 10-800 mg, about 10-500 mg, about 10-300 mg, about 50-800 mg, about 50-500 mg, etc.) of Compound FA. As understood by those skilled in the art, the weight conversion ratio of the meglumine salt of Compound FA to Compound FA is about 1.4107:1, thus, 100 mg free acid (Compound FA) equals about 141.07 mg the meglumine salt. For example, in some embodiments, the pharmaceutical composition comprises the meglumine salt of Compound FA in an amount equivalent to about 10 mg to about 800 mg (e.g., about 10 mg, about 50 mg, about 100 mg, about 150 mg, about 200 mg, about 300 mg, about 400 mg, about 500 mg, about 600 mg, about 700 mg, about 800 mg, or any range between the recited values) of Compound FA. In some embodiments, the pharmaceutical composition comprises the meglumine salt of Compound FA in an amount equivalent to about 10 mg to about 500 mg (e.g., about 10 mg, about 20 mg, about 50 mg, about 100 mg, about 150 mg, about 200 mg, about 300 mg, about 400 mg, about 500 mg, or any range between the recited values) of Compound FA. In some embodiments, the pharmaceutical composition comprises the meglumine salt of Compound FA in an amount equivalent to about 10 mg to about 300 mg (e.g., about 10 mg, about 20 mg, about 30 mg, about 40 mg, about 50 mg, about 60 mg, about 70 mg, about 80 mg, about 90 mg, about 100 mg, about 120 mg, about 140 mg, about 160 mg, about 180 mg, about 200 mg, about 220 mg, about 240 mg, about 260 mg, about 280 mg, about 300 mg, or any range between the recited values) of Compound FA. In some embodiments, the pharmaceutical composition comprises the meglumine salt of Compound FA in an amount equivalent to about 10 mg, about 20 mg, about 30 mg, about 40 mg, about 50 mg, about 75 mg, about 100 mg, about 150 mg, about 200 mg, about 250 mg, about 300 mg, about 400 mg, or about 500 mg, or any range between the recited values, of Compound FA.

The pharmaceutical composition typically comprises the meglumine salt of Compound FA in crystalline form I. In some embodiments, the pharmaceutical composition is free or substantially free of Compound FA in free acid form. However, in some embodiments, the pharmaceutical composition can also include Compound FA in free acid form (other than and in addition to any amount that may exist through equilibrium). In some embodiments, the pharmaceutical composition is free or substantially free of Compound FA in a salt form other than meglumine salt. In some embodiments, the pharmaceutical composition is free or substantially free of meglumine salt of Compound FA in a crystalline form other than Form I. In some embodiments, the pharmaceutical composition comprises meglumine salt of Compound FA in an amorphous form. In some embodiments, the pharmaceutical composition comprises meglumine salt of Compound FA in form I, an amorphous form, or a combination thereof. In some embodiments, the pharmaceutical composition can also comprise the meglumine salt of Compound FA in crystalline form I, II, III, an amorphous form, or in any combination. In any of the embodiments described herein, unless contrary from context, the pharmaceutical composition can comprise or prepared from micronized meglumine salt of Compound FA (e.g., described herein), which for example can have a $D_{90}$ less than 500 μm, such as less than 200 μm or less than 20 μm.

The pharmaceutical composition typically also includes one or more pharmaceutically acceptable excipients, such as a surfactant, binder, diluent, disintegrant, lubricant, etc. For example, in some embodiments, the pharmaceutical composition includes a surfactant, such as sodium lauryl sulfate. In any of the embodiments described herein, unless contrary from context, the pharmaceutical composition can comprise a meglumine salt of Compound FA (e.g., described herein) and a surfactant (e.g., described herein), for example, sodium lauryl sulfate. In some embodiments, the pharmaceutical composition comprises (or is prepared from) a micronized meglumine salt of Compound FA (e.g., described herein) and a surfactant (e.g., described herein), for example, sodium lauryl sulfate. In some embodiments, the micronized meglumine salt of Compound FA can have a $D_{90}$ less than 500 μm, such as less than 200 μm or less than 20 μm. In some embodiments, the pharmaceutical composition comprises a diluent, such as microcrystalline cellulose and/or mannitol. In some embodiments, the pharmaceutical composition comprises microcrystalline cellulose and mannitol, for example, in a weight ratio of microcrystalline cellulose to mannitol of about 1:5 to about 5:1, preferably, mannitol is in a larger amount, for example, the weight ratio of microcrystalline cellulose to mannitol is about 1:1, about 1:2, about 1:3, about 1:4, about 1:5, or any ranges between the recited values. In some embodiments, the pharmaceutical composition comprises a disintegrant, such as crospovidone, such as crospovidone XL-10, or sodium croscarmellose, etc. In some embodiments, the pharmaceutical composition comprises a binder, e.g., povidone, such as povidone K30. In some embodiments, the pharmaceutical composition comprises a lubricant, such as sodium stearyl fumarate or magnesium stearate. Suitable amounts of the excipients are not particularly limited. For example, in some embodiments, the pharmaceutical composition can include a) the meglumine salt of Compound FA in an amount of about 10% to about 80% (e.g., about 10%, about 20%, about 30%, about 40%, about 50%, about 60%, about 70%, about 80%, or any ranges between the recited values, such as about 10-70%, about 10-60%, about 20-50%, etc.) by weight; b) a surfactant (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 2-7%, etc.) by weight; c) a diluent (e.g., described herein) in an amount of about 15% to about 70% (e.g., about 15%, about 20%, about 30%, about 40%, about 50%, about 60%, about 70%, or any ranges between the recited values, such as about 20-50%, about 30-70%, etc.) by weight; d) a binder (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 2-6%, etc.) by weight; e) a disintegrant (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 3-8%, etc.) by weight, and f) a lubricant (e.g., described herein) in an amount of about 0.1% to about 5% (e.g., about 0.1%, about 0.3%, about 0.5%, about 0.7%, about 1%, about 1.5%, about 2%, about 2.5%, about 3%, about 3.5%, about 4%, about 4.5%, about 5%, or any ranges between the recited values, such as about 0.5-1.5%, about 0.5-2.5%, etc.) by weight.

The pharmaceutical composition is typically formulated as an immediate release formulation. For example, in a typical embodiment, the pharmaceutical composition can release substantially all of the meglumine salt of Compound FA in about 60 minutes when tested in a dissolution test using the paddle method (Chinese Pharmacopoeia <0931>, method 2, paddle) at 50 rpm, 900 ml medium (0.5% Sodium dodecyl sulfate (or sodium lauryl sulfate, SDS) in water). In some embodiments, the pharmaceutical composition can release 80% or more of the meglumine salt of Compound FA in about 45 minutes when tested in a dissolution test using the paddle method (Chinese Pharmacopoeia <0931>, method 2, paddle) at 50 rpm, 900 ml medium (0.5% SDS in water).

Tablets

Some embodiments of the present disclosure are directed to tablets comprising Compound FA or a pharmaceutically acceptable salt thereof. In some embodiments, the tablet comprises an amine salt of Compound FA.

In some specific embodiments, the tablet comprises a meglumine salt of Compound FA. In some embodiments, the tablet can be coated. For example, in some embodiments, the tablet can be coated with a coating comprising polyvinyl alcohol. In some embodiments, the coating can further comprise a pigment such as iron oxide (yellow). In some embodiments, the coating comprises polyvinyl alcohol, titanium dioxide, polyethylene glycol, talc powder, and yellow iron oxide. The coating weight gain is typically about 1% to about 5% of the tablet (core), such as about 1%, about 2%, about 3%, about 3.5%, about 4%, or about 5%. As coating may influence dissolution profile of the tablet, it is generally preferred not to include a coating at a coating weight gain above 5%, although in some embodiments, the coating weight gain can also be higher than 5%.

Typically, the tablet herein comprises one or more pharmaceutically acceptable excipients, such as a surfactant, binder, diluent, disintegrant, lubricant, etc. In some embodiments, the tablet comprises a) the meglumine salt of Compound FA in an amount of about 10% to about 80% (e.g., about 10%, about 20%, about 30%, about 40%, about 50%, about 60%, about 70%, about 80%, or any ranges between the recited values, such as about 10-70%, about 10-60%, about 20-50%, etc.) by weight; b) a surfactant (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 2-7%, etc.) by weight; c) a diluent (e.g., described herein) in an amount of about 15% to about 70% (e.g., about 15%, about 20%, about 30%, about 40%, about 50%, about 60%, about 70%, or any ranges between the recited values, such as about 20-50%, about 30-70%, etc.) by weight; d) a binder (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 2-6%, etc.) by weight; e) a disintegrant (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 3-8%, etc.) by weight, and f) a lubricant (e.g., described herein) in an amount of about 0.1% to about 5% (e.g., about 0.1%, about 0.3%, about 0.5%, about 0.7%, about 1%, about 1.5%, about 2%, about 2.5%, about 3%, about 3.5%, about 4%, about 4.5%, about 5%, or any ranges between the recited values, such as about 0.5-1.5%, about 0.5-2.5%, etc.) by weight.

The tablet typically comprises the meglumine salt of Compound FA in crystalline form I. In some embodiments, the tablet is free or substantially free of Compound FA in free acid form. However, in some embodiments, the tablet can also include Compound FA in free acid form (other than and in addition to any amount that may exist through equilibrium). In some embodiments, the tablet is free or substantially free of Compound FA in a salt form other than meglumine salt. In some embodiments, the tablet is free or substantially free of meglumine salt of Compound FA in a crystalline form other than Form I. In some embodiments, the tablet comprises meglumine salt of Compound FA in an amorphous form. In some embodiments, the tablet comprises meglumine salt of Compound FA in form I, an amorphous form, or a combination thereof. In some embodiments, the tablet can also comprise the meglumine salt of Compound FA in crystalline form I, II, III, an amorphous form, or in any combination.

The tablet typically comprises the meglumine salt of Compound FA in an amount equivalent to about 5 mg to about 1.2 grams (e.g., about 10 mg, about 50 mg, about 100 mg, about 200 mg, about 300 mg, about 500 mg, about 750 mg, about 800 mg, about 1000 mg, about 1200 mg, or any ranges between the recited values such as about 10-1000 mg, about 10-800 mg, about 10-500 mg, about 10-300 mg, about 50-800 mg, about 50-500 mg, etc.) of Compound FA. The tablets are typically prepared in unit dosage forms. Each tablet is typically formulated to have certain dosing strength, i.e., containing certain amount of active ingredients. For example, in some embodiments, a single tablet can comprise the meglumine salt of Compound FA in an amount equivalent to about 5 mg to about 1.2 grams, e.g., exemplified herein, such as about 10 mg to about 500 mg of Compound FA. In some embodiments, a single tablet can comprise the meglumine salt of Compound FA in an amount equivalent to about 10 mg to about 800 mg (e.g., about 10 mg, about 50 mg, about 100 mg, about 150 mg, about 200 mg, about 300 mg, about 400 mg, about 500 mg, about 600 mg, about 700 mg, about 800 mg, or any range between the recited values) of Compound FA. In some embodiments, a single tablet can comprise the meglumine salt of Compound FA in an amount equivalent to about 10 mg to about 500 mg (e.g., about 10 mg, about 20 mg, about 50 mg, about 100 mg, about 150 mg, about 200 mg, about 300 mg, about 400 mg, about 500 mg, or any range between the recited values) of Compound FA. In some embodiments, a single tablet can comprise the meglumine salt of Compound FA in an amount equivalent to about 10 mg to about 300 mg (e.g., about 10 mg, about 20 mg, about 30 mg, about 40 mg, about 50 mg, about 60 mg, about 70 mg, about 80 mg, about 90 mg, about 100 mg, about 120 mg, about 140 mg, about 160 mg, about 180 mg, about 200 mg, about 220 mg, about 240 mg, about 260 mg, about 280 mg, about 300 mg, or any range between the recited values) of Compound FA. In some embodiments, a single tablet can comprise the meglumine salt of Compound FA in an amount equivalent to about 10 mg, about 20 mg, about 30 mg, about 40 mg, about 50 mg, about 75 mg, about 100 mg, about 150 mg, about 200 mg, about 250 mg, about 300 mg, about 400 mg, or about 500 mg, or any range between the recited values, of Compound FA. Typically, to achieve a desired therapeutically effective amount, one or more tablets can be used.

Various surfactants are suitable to be included in the tablets herein. In some embodiments, the surfactant can include a non-ionic surfactant, such as ethyleneoxide/propyleneoxide copolymers or poloxamers, such as poloxamer 124, poloxamer 188, poloxamer 237, poloxamer 338 or poloxamer 407, polyethoxylated castor oils such as those sold under the brand name Cremophor® RH40, ethoxylated polysorbates, such as polysorbate 20, polysorbate 40, polysorbate 60 and polysorbate 80 sold respectively under the brand names Tween® 20, Tween® 40, Tween® 60 and Tween® 80, or alternatively polyethylene hydroxystearates such as polyethylene hydroxystearate 660 sold under the brand name Solutol® H515. In some embodiments, the surfactant can include an ionic surfactant such as a cationic surfactant or an anionic surfactant, such as sodium lauryl sulfate. Other suitable surfactants include any of those described herein. In any of the embodiments described herein, unless specified or otherwise contradictory from context, the surfactant can comprise, consist essentially of, or consists of sodium lauryl sulfate.

Various diluents are suitable to be included in the tablets herein. Non-limiting useful diluents include for example, various saccharides such as sucrose, lactose, polysaccharides such as starches, e.g., starch pregelantised, cellulose (e.g., microcrystalline cellulose), cellulose ethers, sugar alcohols such as xylitol, sorbitol, or mannitol, proteins such as gelatin, talc, etc. In some specific embodiments, the tablet comprises microcrystalline cellulose and/or mannitol. In some embodiments, the tablet comprises microcrystalline cellulose and mannitol, for example, in a weight ratio of microcrystalline cellulose to mannitol of about 1:5 to about 5:1, preferably, mannitol is in a larger amount, for example, the weight ratio of microcrystalline cellulose to mannitol is about 1:1, about 1:2, about 1:3, about 1:4, about 1:5, or any ranges between the recited values. Other suitable diluents include any of those described herein. In any of the embodiments described herein, unless specified or otherwise contradictory from context, the diluent can comprise, consist essentially of, or consists of microcrystalline cellulose and/or mannitol, e.g., in a ratio described herein.

Binders suitable for the tablets herein are not particularly limited. Non-limiting useful binders include various saccharides such as sucrose, lactose, polysaccharides such as alginic acid/alginate, wax, starches such as corn starch, potato starch, etc., cellulose, cellulose ethers, sugar alcohols such as xylitol, sorbitol, or mannitol, proteins such as gelatin, and other polymers such as polyvinylpyrrolidone (povidone), copovidone, polyethylene glycol, etc. For example, in some embodiments, the binder can comprise a povidone, such as povidone K30. Other suitable binders include any of those described herein. In any of the embodiments described herein, unless specified or otherwise contradictory from context, the binder can comprise, consist essentially of, or consists of povidone, such as povidone K30.

Disintegrants suitable for the tablets herein are also not particularly limited. In some embodiments, the tablet comprises crospovidone, such as crospovidone XL-10. In some embodiments, the tablet comprises sodium croscarmellose. Other suitable disintegrants (disintegrating agents) include any of those described herein. In any of the embodiments described herein, unless specified or otherwise contradictory from context, the disintegrant can comprise, consist essentially of, or consists of crospovidone, such as crospovidone XL-10 or sodium croscarmellose.

Various lubricants are also suited for use in the tablets herein. In some embodiments, the lubricant can be stearic acid or a salt thereof. In some embodiments, the tablet comprises magnesium stearate. In some embodiments, the tablet comprises sodium stearyl fumarate. Other suitable lubricants include any of those described herein. In any of the embodiments described herein, unless specified or otherwise contradictory from context, the lubricant can comprise, consist essentially of, or consists of magnesium stearate or sodium stearyl fumarate.

To be clear, some excipients may have more than one function. For clarity of calculation of weight percentages, as used herein, when a dual (or multiple) functional agent is included in a pharmaceutical composition such as tablet or granule herein, the amount of that agent is proper as long as it can fit into one of the specified weight limits according to one of its functions, unless otherwise obvious from context.

The tablets can also include other commonly used excipients such as flavoring agents, coloring agents, preservatives, sweeteners, antioxidants, etc. These excipients are within the knowledge of those skilled in the art, and can be found, for example, in the Handbook of Pharmaceutical Excipients ($7^{th}$ Ed. 2012).

In any of the embodiments described herein, unless specified or otherwise contrary from context, the pharmaceutical composition/tablets can be any of those having the ingredients shown in Tables 8A, 8C, or 8D herein in substantially the same amount or substantially the same percentages, e.g., within 20% or within 10% of the respective values shown therein, or any of those produced by the methods described in the Examples section.

The tablets herein can be prepared by any suitable methods, such as direct compression, dry granulation, or wet granulation, which typically can include weighing, milling, mixing, granulation, drying, compaction, optionally coating and packaging. In some embodiments, the tablet is prepared by a process comprising wet granulation. In some embodiments, the tablet is prepared by a process comprising compressing granules thereby forming the tablet. The granules typically comprise the meglumine salt of Compound FA, surfactant, diluent, binder, and disintegrant, e.g., as described herein. For example, in some embodiments, the tablet is prepared by a process comprising compressing granules for tablet formation, wherein the granules comprise the meglumine salt of Compound FA, sodium lauryl sulfate, microcrystalline cellulose, mannitol, povidone, and/or crospovidone, the amount of which can be any of those described herein in any combination. In some embodiments, the granules can be further mixed with a lubricant before being compressed into the tablet.

The tablets herein typically prepared with acceptable physical properties and dissolution profiles. For example, the tablets herein typically have a hardness of about 30-200 N, such as about 80 N to about 140 N. The tablets herein typically also have a friability of less than 1%, such as less than 0.5% (4 minutes, 100 revolutions). Thickness of the tablets can be adjusted, for example, to about 3-10 mm, such as about 5-6 mm.

The tablets herein typically have an immediate release profile. For example, in some embodiments, the tablet can release substantially all of the meglumine salt of Compound FA in about 60 minutes when tested in a dissolution test using the paddle method (Chinese Pharmacopoeia <0931>, method 2, paddle) at 50 rpm, 900 ml medium (0.5% Sodium dodecyl sulfate (or sodium lauryl sulfate, SDS) in water). In some embodiments, the pharmaceutical composition can release 80% or more of the meglumine salt of Compound FA in about 45 minutes when tested in a dissolution test using the paddle method (Chinese Pharmacopoeia <0931>, method 2, paddle) at 50 rpm, 900 ml medium (0.5% SDS in water).

The tablets herein typically are storage stable for at least 1 month, such as 1, 3, 6, 12 months or longer. For example, when stored under the conditions of (1) 60° C.; (2) 25° C./92.5% RH; (3) 40° C./75% RH; or (4) light ($1.2\times10^6$ Lux·hr/200 w·hr/m2), the tablets herein (directly exposed or in a package container such as HDPE bottle with PP cap as described herein) can be stable for at least 1 month, e.g., with no significant change in appearance, drug content and related substance, when compared to initial.

Granules

In some embodiments, the present disclosure also provides a granule, which can be useful, for example, for preparing the tablet herein or a capsule formulation. The granule can be wet or dry (e.g., with moisture content less than 5% by weight, such as less than 3%). The granule typically comprises Compound FA or a pharmaceutically acceptable salt thereof. In some embodiments, the granule comprises an amine salt of Compound FA.

In some specific embodiments, the granule comprises a meglumine salt of Compound FA. Typically, the granule also comprises one or more pharmaceutically acceptable excipients, such as a surfactant, binder, diluent, disintegrant, lubricant, etc. In some embodiments, the granule comprises a) the meglumine salt of Compound FA in an amount of about 10% to about 80% (e.g., about 10%, about 20%, about 30%, about 40%, about 50%, about 60%, about 70%, about 80%, or any ranges between the recited values, such as about 10-70%, about 10-60%, about 20-50%, etc.) by weight; b) a surfactant (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 2-7%, etc.) by weight; c) a diluent (e.g., described herein) in an amount of about 15% to about 70% (e.g., about 15%, about 20%, about 30%, about 40%, about 50%, about 60%, about 70%, or any ranges between the recited values, such as about 20-50%, about 30-70%, etc.) by weight; d) a binder (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 2-6%, etc.) by weight; and e) a disintegrant (e.g., described herein) in an amount of about 0.1% to about 10% (e.g., about 0.5%, about 1%, about 2%, about 3%, about 4%, about 5%, about 6%, about 7%, about 8%, about 10%, or any ranges between the recited values, such as about 1-8%, about 3-8%, etc.) by weight.

The granule typically comprises the meglumine salt of Compound FA in crystalline form I. In some embodiments, the granule is free or substantially free of Compound FA in free acid form. In some embodiments, the granule is free or substantially free of Compound FA in a salt form other than meglumine salt. In some embodiments, the granule is free or substantially free of meglumine salt of Compound FA in a crystalline form other than Form I. In some embodiments, the granule comprises meglumine salt of Compound FA in an amorphous form. In some embodiments, the granule comprises meglumine salt of Compound FA in form I, an amorphous form, or a combination thereof. In some embodiments, the granule can also comprise the meglumine salt of Compound FA in crystalline form I, II, III, an amorphous form, or in any combination.

Various surfactants are suitable to be included in the granules herein. In some embodiments, the granule can include sodium lauryl sulfate.

Various diluents are suitable to be included in the granules herein. In some specific embodiments, the granule comprises microcrystalline cellulose and/or mannitol. In some embodiments, the granule comprises microcrystalline cellulose and mannitol, for example, in a weight ratio of microcrystalline cellulose to mannitol of about 1:5 to about 5:1, preferably, mannitol is in a larger amount, for example, the weight ratio of microcrystalline cellulose to mannitol is about 1:1, about 1:2, about 1:3, about 1:4, about 1:5, or any ranges between the recited values.

Binders suitable for the granules herein are not particularly limited. For example, in some embodiments, the binder can comprise a povidone, such as povidone K30.

Disintegrants suitable for the granules herein are also not particularly limited. In some embodiments, the granule comprises crospovidone, such as crospovidone XL-10. In some embodiments, the granule comprises sodium croscarmellose. While the granules herein typically include a disintegrant, in some embodiments, the granule can also not include a disintegrant. For example, the granule can be prepared without intra-granular disintegrant, but is mixed with an extra-granular disintegrant, which can also comprise crospovidone, such as crospovidone XL-10, or sodium croscarmellose.

In some embodiments, the granules herein can also be mixed with a lubricant such as magnesium stearate or sodium stearyl fumarate.

The granules can have various sizes, which do not appear to have a significant impact on dissolution of a tablet made from such granules. Typically, the granules can have a size less than 1 mm.

Method of Preparation

In some embodiments, the present disclosure also provides a method of preparing the tablets herein. In some embodiments, the method can include direct compression, dry granulation, or wet granulation. In some specific embodiments, the tablet is prepared by a process comprising wet granulation.

In some embodiments, the method comprises wet granulating a mixture of a meglumine salt of Compound FA, surfactant, diluent, binder, and disintegrant to form wet granules. In some embodiments, the method further comprises drying the wet granules to form dried granules. In some embodiments, the drying is conducted with fluid bed drying. The moisture content of the dried granules can be controlled, for example, to no more than 5% or no more than 3% water content (by LOD). In some embodiments, the method can further comprising dry milling the dried granules to form dry milled granules. In some embodiments, the method does not include a step of wet milling.

The dry milled granules are typically mixed with an extra-granular disintegrant (e.g., crospovidone, such as crospovidone XL-10) and a lubricant (e.g., described herein) to form lubricated granules. In some embodiments, the lubricated granules are compressed into a tablet core. In some embodiments, the method can further comprise film coating the tablet core to form a coated tablet. In some embodiments, the coating weight gain is about 1% to about 5% of the tablet (core), such as about 1%, about 2%, about 3%, about 3.5%, about 4%, or about 5%. In some embodiments, the coating comprises polyvinyl alcohol. In some embodiments, the coating can further comprising a pigment such as iron oxide (yellow). In some embodiments, the coating comprises polyvinyl alcohol, titanium dioxide, polyethylene glycol, talc powder, and yellow iron oxide.

The amounts of meglumine salt of Compound FA, and the types and amounts of the surfactant, diluent, binder, and disintegrant can include any of those described herein in any combination. For example, in some embodiments, the mixture used for wet granulation comprises the meglumine salt of Compound FA in an amount of about 10% to about 80% by weight; the surfactant in an amount of about 0.1% to about 10% by weight; the diluent in an amount of about 15% to about 70% by weight; the binder in an amount of about 0.1% to about 10% by weight; and the disintegrant in an amount of about 0.1% to about 10% by weight.

The mixture used for wet granulation typically comprises the meglumine salt of Compound FA in crystalline form I. In some embodiments, the mixture is free or substantially free of Compound FA in free acid form. In some embodiments, the mixture is free or substantially free of Compound FA in a salt form other than meglumine salt. In some embodiments, the mixture is free or substantially free of meglumine salt of Compound FA in a crystalline form other than Form I. In some embodiments, the mixture comprises meglumine salt of Compound FA in an amorphous form. In some embodiments, the mixture comprises meglumine salt of Compound FA in form I, an amorphous form, or a combination thereof. In some embodiments, the mixture can also comprise the meglumine salt of Compound FA in crystalline form I, II, III, an amorphous form, or in any combination. In some embodiments, the mixture comprises the meglumine of Compound FA which is micronized and has a D90 of less than 500 μm, such as less than 200 μm or less than 20 μm. In some embodiments, the mixture comprises the meglumine of Compound FA which is not micronized. In some embodiments, the mixture comprises sodium lauryl sulfate. In some embodiments, the mixture comprises microcrystalline cellulose and mannitol. In some embodiments, the mixture comprises a povidone, such as povidone K30. In some embodiments, the mixture comprises crospovidone, such as crospovidone XL-10.

The granules, dried granules, dry milled granules, lubricated granules, tablet cores, and coated tablets produced by any of the methods described herein (including those shown in the Examples section) are also novel compositions of the present disclosure.

Methods of Treatment

The salts of the present disclosure and pharmaceutical compositions described herein are useful in treating and/or preventing proliferative diseases and/or a disease associated with a steroid hormone such as estrogen. As discussed in WO2017/136688, the content of which is hereby incorporated by reference in its entirety, SERDs such as Compound FA induced degradation of ER and inhibited the growth of ER+ breast cancer cells and exhibited better human hepatocyte clearance than drug of the same class such as fulvestrant, as well as those in clinical trials such as GDC-0810 and AZD9496.

Accordingly, in some embodiments, the present disclosure also provides methods of treating a proliferative disease and/or a disease associated with a steroid hormone such as estrogen, in a subject in need thereof, the methods comprising administering to the subject an effective amount (e.g., therapeutically effective amount) of a salt of the present disclosure (e.g., the amine salts of Compound FA, such as Form I, II, or III of meglumine salt of Compound FA or Form A of the lysine salt of Compound FA), or pharmaceutical composition described herein (e.g., the tablets described herein).

In some embodiments, the present disclosure also provide a method of preventing a proliferative disease and/or a disease associated with a steroid hormone such as estrogen, in a subject in need thereof, the methods comprising administering to the subject an effective amount (e.g., prophylactically effective amount) of a salt of the present disclosure (e.g., the amine salts of Compound FA, such as Form I, II, or III of meglumine salt of Compound FA or Form A of the lysine salt of Compound FA), or a pharmaceutical composition described herein.

In certain embodiments, the method is for treating and/or preventing cancer. In certain embodiments, the cancer is breast cancer. In certain embodiments, the method is for treating and/or preventing gynecological disease or cancer associated with ER such as cancer of the ovary, cervix or endometrium and breast cancer, particularly ER+ breast cancer. In some embodiments, the cancer (e.g., breast cancer, such as ER+ breast cancer) is resistant to estrogen modulators such as tamoxifen and/or aromatase inhibitors.

In certain embodiments, the method described herein further includes administering to the subject an additional pharmaceutical agent such as an additional antiproliferative agent. In some embodiments, the antiproliferative agent can be a CDK4/CDK6 inhibitor, such as palbociclib. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent. In certain embodiments, the method described herein further includes radiotherapy, immunotherapy, and/or transplantation (e.g., bone marrow transplantation).

The salts and/or compositions of the present disclosure can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops). Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The effective amount such as therapeutically effective amount of the salt of the present disclosure or pharmaceutical composition herein can be typically delivered to the subject in need thereof by administering one or more unit dosage forms herein, such as one or more tablets of different strength (e.g., each containing 10-800 mg such as 10-500 mg or 10-300 mg equivalent weight of Compound FA). In some embodiments, the effective amount can be delivered by administering to the subject a single unit dosage form, such as a tablet having the desired amount of active ingredients. In some embodiments, the effective amount can be delivered by administering to the subject more than one unit dosage forms, such as 1, 2, 3, or 4 tablets, each having a desired amount of active ingredients, such as 10-800 mg such as 10-500 mg or 10-300 mg equivalent weight of Compound FA. The dosing amount and dosing regimen for the methods herein are not particularly limited. For example, in some embodiments, Compound FA or a pharmaceutically acceptable salt thereof is administered to the subject daily. In some embodiments, the daily dose of Compound FA or a pharmaceutically acceptable salt thereof can be delivered to the subject by a single dose or 2 or 3 equal smaller doses within a day, wherein each dose can be satisfied by one or more unit dosage forms herein (such as one or more tablets herein).

The salts and/or compositions of the present disclosure can be administered in combination with one or more additional pharmaceutical agents (e.g., therapeutically and/or prophylactically active agents) useful in treating and/or preventing a proliferative disease. The salts or compositions can be administered in combination with additional pharmaceutical agents that improve their activity (e.g., activity (e.g., potency and/or efficacy) in treating a proliferative disease in a subject in need thereof, and/or in preventing a proliferative disease in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a salt of the present disclosure and an additional pharmaceutical agent shows a synergistic effect that is absent in a pharmaceutical composition including one of the compound and the additional pharmaceutical agent, but not both.

The salt or composition of the present disclosure can be administered concurrently with, prior to, or subsequent to one or more additional pharmaceutical agents, which may be useful as, e.g., combination therapies in treating and/or preventing a proliferative disease. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease. In certain embodiments, the additional pharmaceutical agent is a pharmaceutical agent useful in preventing a proliferative disease. In certain embodiments, the additional pharmaceutical agent is a pharmaceutical agent approved by a regulatory agency (e.g., the US FDA) for treating and/or preventing a proliferative disease. Each additional pharmaceutical agent may be administered at a dose and/or on a time schedule determined for that pharmaceutical agent. The additional pharmaceutical agents may also be administered together with each other and/or with the salt or composition of the present disclosure in a single dose or administered separately in different doses. The particular combination to employ in a regimen will take into account compatibility of the salt of the present disclosure with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent, for example, an immune-oncology agents (e.g., anti-PD-1 antibody) or cells (e.g., CAR-T cells)). In certain embodiments, the additional pharmaceutical agent is an anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the salts of the present disclosure or pharmaceutical compositions can be administered in combination with an anti-cancer therapy including, but not limited to, targeted therapy (e.g., mTOR signaling pathway inhibitor), cell therapy, surgery, radiation therapy, immunotherapy, and chemotherapy (e.g., docetaxel, doxorubicin).

Definitions

Unless otherwise obvious from context, in any of the embodiments described herein, the compounds/salts herein can exist predominantly (e.g., at least 85%, at least 90%, at least 95%, at least 99%, etc.) in the stereoisomer as drawn, when applicable. For example, in some embodiments, Compound FA herein can have an enantiomeric purity of greater than 85% enantiomeric excess (e.g., greater than 90% ee, greater than 95% ee, or greater than 99% ee); in some embodiments, Compound FA herein can also have a diastereomeric purity of greater than 85% diastereomeric excess (e.g., greater than 90% de, greater than 95% de, or greater than 99% de); and in some embodiments, Compound FA herein can also have substantially E configuration with respect to the acrylic acid double bond, for example, with less than 1%, or non-detectable, Z configuration.

"Salt(s) of the present disclosure" as used herein refers to any salt of Compound FA described herein, preferably, an amine salt of Compound FA described herein, which can be in a solid form, such as one or more crystalline forms described herein (e.g., Form I, II, or III of meglumine salt of Compound FA or Form A of the lysine salt of Compound FA), amorphous form, or any mixture thereof, which can be anhydrous, hydrate, or solvate.

As used herein, the singular form "a", "an", and "the", includes plural references unless it is expressly stated or is unambiguously clear from the context that such is not intended.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

As used herein, the term "about" modifying an amount related to the disclosure refers to variation in the numerical quantity that can occur, for example, through routine testing and handling; through inadvertent error in such testing and handling; through differences in the manufacture, source, or purity of ingredients employed in the disclosure; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a salt of the present disclosure to a subject in need of such treatment.

The term "therapeutically effective amount," as used herein, refers to that amount of a therapeutic agent (e.g., any one or more of the salts of the present disclosure) sufficient to result in amelioration of one or more symptoms of a disorder or condition (e.g., breast cancer such as ER+ breast cancer), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment. In any of the embodiments described herein, the subject can be a human.

EXAMPLES

Example 1. General Methods

Materials: the starting materials, reagents, solvents, etc. are generally available through commercial sources.

$^1H$ NMR was performed using Bruker Advance 300 equipped with automated sample (B-ACS 120).

POWDER X-RAY DIFFRACTION (XRPD): The solid samples were examined using X-ray diffractometer (Bruker D8 advance). The system is equipped with LynxEye detector. The x-ray wavelength is 1.5406 Å. The samples were scanned from 3 to 40° 2θ, at a step size 0.02° 2θ. The tube voltage and current were 40 KV and 40 mA, respectively.

Polarizing microscope analysis (PLM): PLM analysis was conducted on a Nikon Instruments Eclipse 80i. The image was captured by a DS camera and transmitted to the computer. The photo was processed with the NIS-Elements D3.0 software.

TGA ANALYSIS: TGA analysis was carried out on a TA Instruments TGA Q500. Samples were placed in an open tarred aluminum pan, automatically weighed, and inserted into the TGA furnace. The samples were heated at a rate of 10° C./min to final temperature.

DSC ANALYSIS: DSC analysis was conducted on a TA Instruments Q200. The calibration standard was indium. A sample in weight was placed into a TA DSC pan, and weight was accurately recorded. The samples were heated under nitrogen (50 ml/min) at a rate of 10° C./min to a final temperature.

Dynamic moisture sorption analysis (DVS): DVS was determined using IGAsorp (Hiden Isochema, UK). The sample was tested at a targeted RH (relative humidity) of 10 to 90% full cycle in step mode. The analysis was performed in 10% RH increments.

HPLC ANALYSIS: a representative HPLC method is shown below, which can be used, for example, to analyze the purity, solubility, and stability of the salts herein.

| | |
|---|---|
| Instrument | Agilent 1260 series |
| Column | Sunfire C18, 3.5 μm, 4.6*150 mm |
| Column temperature | 40° C. |
| Mobile phase | A: 0.05% TFA in $H_2O$, B: 0.05% TFA in Acetonitrile |
| Gradient condition (% of B) | 0-15 min: 15-85%, 15-25 min: 85% |
| Flow rate | 1.0 mL/min |
| Injection volume | 5 μL |
| UV wavelength | 220 nm |
| Post time | 5 min |

Example 2. Preparation of meglumine (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl acrylate

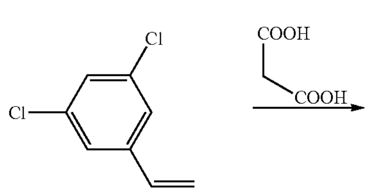

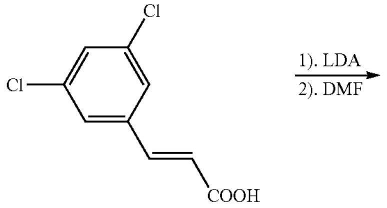

1

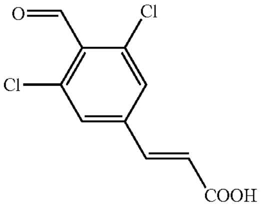

2

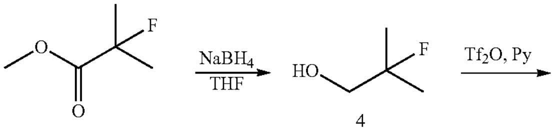

3 4

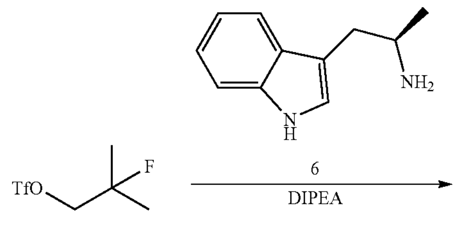

5

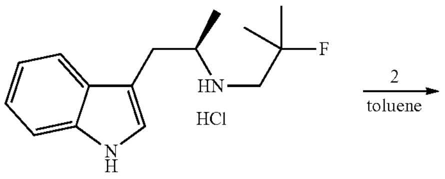

7

-continued

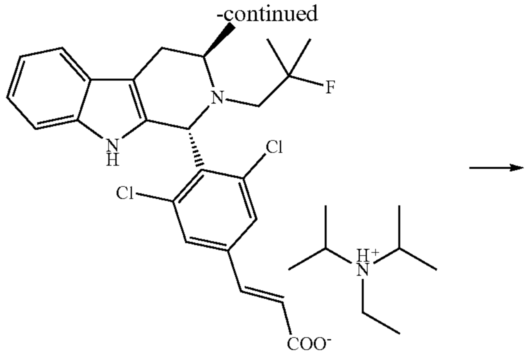

8

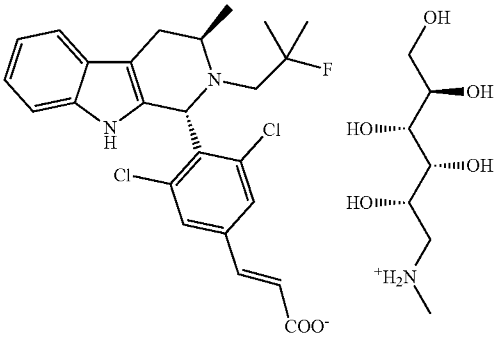

9

A mixture of 3,5-dichlorobenzaldehyde (250.0 g, 1.43 mol), malonic acid (223.0 g, 2.14 mol) and pyridine (250 mL) in DMF (500 mL) was heated at temperatures ranging from 30° C. to 75° C. until the reaction was completed. The mixture was then cooled to 10 to 20° C., and a hydrochloric acid solution (0.6 N, 5 L) was added. The mixture was stirred at 10 to 20° C. for 6 hours and filtered. The filter cake was washed with water, and dried at 40 to 60° C. under vacuum to produce 1 (281 g, 90% yield).

To a solution of 1 (50.0 g, 0.23 mol) in THE (1 L) was added LDA (2.0 M in THF, 290 mL) dropwise at −80 to −60° C. under $N_2$. The mixture was stirred at this temperature range for 0.5 hour, followed by slow addition of DMF (42.0 g, 0.58 mol). The resulting mixture was stirred at −70 to −50° C. until the reaction was completed. Water (10 mL) and hydrochloric acid (2.0 M, 900 mL) were added sequentially. The organic layer was separated, washed with an aqueous NaCl solution (5%, 250 mL) and concentrated to 200 mL. To the residue was added DCM (50 mL), and the resulting slurry was stirred at 20 to 30° C. for 6 hours and filtered. The filter cake was dried at 30 to 40° C. under vacuum to produce 2 (36.1 g, 64% yield).

To a suspension of $NaBH_4$ (16.5 g, 0.44 mol) in THE (120 mL) was added 3 (40.0 g, 0.33 mol) in several portions maintaining the reaction temperature at 35 to 45° C. under $N_2$. The mixture was stirred at 35 to 45° C. until the reaction was completed. An aqueous $KHCO_3$ solution (20%, 80 L) and DCM (400 mL) were added, and the resulting mixture was filtered. The organic layer was separated, washed with aqueous NaCl (20%, 200 mL), dried over 4 Å molecular sieves (24 g) and filtered to produce a solution of crude 4 in DCM. To the solution of 4 in DCM was added pyridine (52.7 g, 0.67 mol), followed by slow addition of $Tf_2O$ (98.7 g, 0.35 mol) maintaining the reaction temperatures at −10 to 0° C. The mixture was stirred at 0 to 10° C. until the reaction was completed. Water (400 mL) was added, and the organic layer was separated, washed with aqueous $NaHCO_3$ (6.5%, 400 mL) and aqueous NaCl (20%, 200 mL) solutions sequentially, and concentrated to produce 5 (57.7 g, 78% yield).

To a solution of 6 (20.0 g, 0.115 mol) and DIPEA (19.3 g, 0.149 mol) in MeCN (200 mL) was added 5 (40.0 g, 0.178 mol), and the mixture was heated at 65 to 75° C. under $N_2$ until the reaction was completed. The reaction mixture was concentrated at 20 to 30° C. under vacuum, followed by addition of EtOAc (300 mL). The resulting mixture was washed with an aqueous $NaHCO_3$ solution (6.5%, 200 L), water (2×100 L), and concentrated. To the crude residue was added MeCN (40 mL) and EtOAc (20 mL), followed by a hydrogen chloride solution (4.0 M in EtOAc, 40 mL) at −5 to 5° C. The mixture was stirred at −5 to 5° C. for 8 hours and filtered. The filter cake was washed with EtOAc (65 L), and dried at 50 to 65° C. under vacuum to produce 7 (23.9 g, 73% yield).

To a suspension of 7 (12.8 g, 0.045 mol) in toluene (250 mL) was added an aqueous $Na_2CO_3$ solution (13%, 208 g), and the mixture was stirred for 0.5 hour. The organic layer was separated. To the organic layer was added DIPEA (3.64 g) and 2 (10 g, 0.041 mol), and the mixture was heated at 100 to 120° C. under $N_2$ until the reaction was completed. The mixture was cooled to 45-55° C., followed by addition of seed crystals of 8 and EtOAc (200 mL). A solvent switch from toluene to EtOAc was performed by distillation with additional amounts of EtOAc (2×250 mL) to a slurry, followed by addition of DIPEA (5.2 g). The slurry was stirred at 15 to 25° C. for 12 hours and filtered. The filtered cake was washed with a mixed solvent of EtOAc (28 mL) and toluene (12 mL), and dried at 35 to 45° C. under vacuum to produce 8 (18.0 g, 73% yield).

To a suspension of 8 (17.5 g, 0.029 mol) in EtOAc (315 mL) was added an aqueous citric acid solution (1.5%, 226 mL). The mixture was stirred for 1 hour, and the layers were separated. The organic layer was washed with an aqueous citric acid solution (0.1%, 262 mL), water (2×175 mL), and concentrated to a low volume of 35 mL. To the concentrate was added methanol (210 mL), followed by an aqueous meglumine solution (20%, 26.2 g) and seed crystals of 9. The mixture was stirred at 15 to 25° C. for 2 hours, and then additional amount of the aqueous meglumine solution (20%, 8.8 g) was added. The mixture was then stirred at 15 to 25° C. for 16 hours and filtered. The filtered cake was washed with a mixed solution of MeOH and water (6:1, 70 mL), and dried at 46 to 65° C. under vacuum to produce 9 (15.2 g, 78% yield), which is in crystalline Form I. HRMS System showed ion peak of $[M+H]^+$: m/z 475.1348.

The following table shows the proton NMR and its assignments of 9:

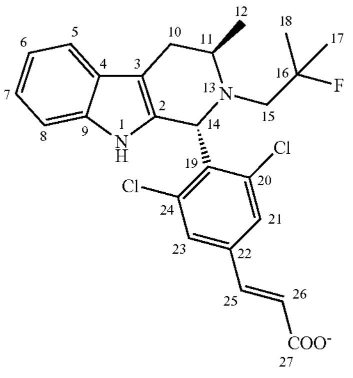

-continued

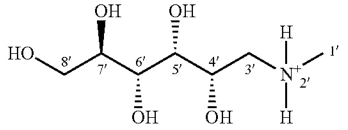

| Chemical Shift (δ) ppm* | Multiplicity† | Approximate integration # of proton | Assignment or resonance # |
|---|---|---|---|
| 10.38 | s | 1H | NH-1 |
| 7.79 | d (J = 1.2 Hz) | 1H | H-21/23 |
| 7.52 | brs | 1H | H-23/21 |
| 7.39 | d (J = 7.2 Hz) | 1H | H-5 |
| 7.24 | d (J = 16.0 Hz) | 1H | H-25 |
| 7.16 | d (J = 8.0 Hz) | 1H | H-8 |
| 6.97 | td (J = 7.2, 1.2 Hz) | 1H | H-7 |
| 6.92 | td (J = 7.2, 1.2 Hz) | 1H | H-6 |
| 6.59 | d (J = 16.0 Hz) | 1H | H-26 |
| 5.58 | s | 1H | H-14 |
| 3.86 | m | 1H | H-4' |
| 3.72 | t (J = 5.2 Hz) | 1H | H-11 |
| 3.67 | dd (J = 5.2, 1.2 Hz) | 1H | H-5' |
| 3.59 | dd (J = 10.8, 3.2 Hz) | 1H | H-8'a |
| 3.50 | m | 1H | H-6' |
| 3.43 | overlap | 1H | H-7' |
| 3.40 | t (J = 5.2 Hz) | 1H | H-8'b |
| 3.08 | brd (J = 14.4 Hz) | 1H | H-10a |
| 2.96 | overlap | 1H | H-15a |
| 2.95 | overlap | 1H | H-3'a |
| 2.85 | dd (J = 12.4, 8.4 Hz) | 1H | H-3'b |
| 2.63 | d (J = 14.4 Hz) | 1H | H-10b |
| 2.47 | s | 3H | H-1' |
| 2.23 | dd (J = 29.2, 14.4 Hz) | 1H | H-15b |
| 1.13 | d (J = 21.6 Hz) | 3H | H-17/18 |
| 1.10 | d (J = 21.6 Hz) | 3H | H-18/17 |
| 1.05 | d (J = 6.4 Hz) | 3H | H-12 |

*Referenced to DMSO-$d_6$ at δ = 2.50 ppm

†s: singlet; d: doublet; t: triplet; m: multiplet; dd: double doublet; td: triple doublet; brs: broad singlet; brd: broad doublet Procedure of preparing seed crystals of 8: To a suspension of 7 (128 g, 0.45 mol) in toluene (2.5 L) was added an aqueous $Na_2CO_3$ solution (13%, 2080 g), and the mixture was stirred for 0.5 hour. The organic layer was separated. To the organic layer was added DIPEA (36.4 g) and 2 (100 g, 0.41 mol), and the mixture was heated at 100 to 120° C. under $N_2$ until the reaction was completed. The mixture was cooled to 45-55° C. Distillation of toluene was performed with additional amounts of EtOAc (2×2.5 L) to a slurry, followed by addition of DIPEA (52 g). The slurry was stirred at 15 to 25° C. for no less than 12 hours and filtered. The filtered cake was washed with a mixture of EtOAc (280 mL) and toluene (120 mL), and dried at 35 to 45° C. under vacuum to produce 8 (180.5 g, 73% yield) used as seed crystals. Representative XRPD and DSC spectra of the crystal form 8 are shown in FIGS. 6A and 6B.

Procedure of preparing seed crystals of 9: To a suspension of 8 (8.7 g, 0.014 mol) in EtOAc (157 mL) was added an aqueous citric acid solution (1.5%, 112 mL). The mixture was stirred for 1 hour, and the layers were separated. The organic layer was washed with an aqueous citric acid solution (0.1%, 130 mL), water (2×87 mL), and concentrated to a low volume of about 17 mL. To the concentrate was added methanol (104 mL), followed by an aqueous meglumine solution (20%, 13.0 g). The mixture was stirred at 15 to 25° C. for 2 hours, and then additional amount of the aqueous meglumine solution (20%, 4.4 g) was added. The mixture was then stirred at 15 to 25° C. for no less than 16 hours and filtered. The filtered cake was washed with a mixture of MeOH and water (6:1, 35 mL), and dried at 46 to 65° C. under vacuum to produce 9 (7.6 g, 78% yield) used as seed crystals (Form I).

Example 3. Meglumine Salt of Compound FA Polymorphs and Interconversion

Meglumine salt of Compound FA was prepared and used as initial material (Form I) for polymorph screening. Screening was conducted using single and binary solvent mixtures by various crystallization methods, such as solvent crystallization, precipitation, slurry, evaporation and diffusion method. Thermal and mechanical treatments were also performed to explore additional crystal form.

Solid samples obtained were characterized by X-ray powder diffractermeter (XRPD), differential scanning calorimeter (DSC), thermogravimetric analyzer (TGA) and polarized microscopy (PLM).

Two crystal forms (Form I, II) and dihydrate were identified and prepared in the screening. Interconversion studies of different forms and dihydate were performed in water and IPA at room temperature and 60° C. Results showed that dihydrate was the most stable in water at room temperature, and Form I was the most stable crystal form in IPA (room temperature and 60° C.) and in water at 60° C. In addition, crystal form of Form I remained unchanged after storage at 92.5% RH for 10 days.

Example 3A. Form I of the Meglumine Salt

Preparation of Form I: 1.08536 g of meglumine was added into 50 mL of methanol with stirring at room temperature. The solid sample was almost dissolved after added another 30 mL of methanol with stirred for 20 min. Added 2.6 g of Compound FA, and then the solution became clear. Precipitation occurred 25 min later. The suspension was concentrated to dry after 1 h. Added 20 mL of IPA and kept stirring at room temperature overnight. Then added 30 mL of IPA and stirred for 2 hours. The sample was collected by filtration. After characterization, the sample was used as initial material for polymorph screening.

Physical treatment of Form I: Form I of meglumine salt was grinded for 2 min and 5 min. After grinding, the crystallinity declined, but the crystal form was still Form I.

Characterization of Form C The sample was rodlike crystal. TGA and DSC profiles showed that there was about 0.200 weight loss prior to decomposition, and an endothermic peak with onset temperature of 224.83° C. The sample was named as Form L. Representative XRPD and DSC spectra are shown in FIGS. 1A-1B. A table of XRPD peaks are shown below in Table 1.

TABLE 1

XRPD peak tables for Form I.

| Angle 2-Theta ° | Intensity % % | d value Angstrom | Intensity Count |
|---|---|---|---|
| 4.705 | 58.5 | 18.76671 | 1235 |
| 9.054 | 45.8 | 9.7593 | 966 |
| 9.95 | 85.4 | 8.88233 | 1802 |
| 10.248 | 11.9 | 8.62498 | 252 |
| 11.02 | 16.5 | 8.02203 | 349 |
| 11.288 | 22 | 7.83245 | 464 |
| 12.234 | 8.9 | 7.22857 | 187 |
| 12.915 | 23.9 | 6.84911 | 505 |
| 13.28 | 28.7 | 6.66177 | 605 |
| 13.493 | 22.3 | 6.55701 | 471 |

TABLE 1-continued

XRPD peak tables for Form I.

| Angle 2-Theta ° | Intensity % % | d value Angstrom | Intensity Count |
|---|---|---|---|
| 13.761 | 9.9 | 6.43003 | 209 |
| 14.136 | 19.1 | 6.2604 | 402 |
| 14.746 | 7.4 | 6.00253 | 157 |
| 15.077 | 20.9 | 5.87157 | 441 |
| 15.517 | 6.6 | 5.70587 | 140 |
| 16.352 | 28.9 | 5.41663 | 609 |
| 16.741 | 12.7 | 5.29152 | 268 |
| 17.579 | 76.7 | 5.04099 | 1618 |
| 18.22 | 38.7 | 4.86526 | 817 |
| 18.776 | 27.5 | 4.72233 | 581 |
| 18.967 | 53.4 | 4.67508 | 1127 |
| 19.431 | 10.5 | 4.56456 | 222 |
| 20.018 | 29.7 | 4.43201 | 627 |
| 20.383 | 20.9 | 4.35348 | 440 |
| 20.981 | 18.9 | 4.23083 | 398 |
| 21.52 | 100 | 4.1259 | 2110 |
| 22.039 | 13.4 | 4.0299 | 283 |
| 22.415 | 23.4 | 3.96315 | 494 |
| 23.268 | 18.8 | 3.81976 | 397 |
| 23.654 | 40.8 | 3.75832 | 860 |
| 23.916 | 20.4 | 3.7177 | 431 |
| 24.292 | 11.1 | 3.66101 | 235 |
| 24.886 | 23.6 | 3.57504 | 499 |
| 25.312 | 22.8 | 3.51577 | 481 |
| 26.296 | 18 | 3.38644 | 379 |
| 26.592 | 8.2 | 3.34944 | 172 |
| 26.91 | 10.1 | 3.31058 | 214 |
| 27.226 | 12.8 | 3.27283 | 271 |
| 27.755 | 9.4 | 3.21163 | 198 |
| 28.466 | 15.3 | 3.13302 | 323 |
| 28.786 | 9.5 | 3.09887 | 201 |
| 29.319 | 14.6 | 3.04379 | 308 |
| 29.64 | 11.3 | 3.01158 | 239 |
| 30.037 | 13.8 | 2.9726 | 291 |
| 30.86 | 6 | 2.8952 | 127 |
| 31.481 | 11.8 | 2.83946 | 250 |
| 31.828 | 8.9 | 2.80933 | 188 |
| 32.39 | 7.3 | 2.76183 | 155 |
| 32.861 | 9 | 2.72333 | 189 |
| 33.054 | 12.6 | 2.70787 | 265 |
| 33.805 | 10.6 | 2.64942 | 223 |
| 34.238 | 10.4 | 2.61686 | 219 |
| 34.839 | 8.6 | 2.57311 | 181 |
| 35.157 | 8.4 | 2.55054 | 178 |
| 35.936 | 13.3 | 2.49704 | 280 |
| 36.318 | 12.4 | 2.47168 | 261 |
| 36.924 | 14.6 | 2.43245 | 309 |
| 37.393 | 18.6 | 2.40304 | 393 |
| 37.683 | 11.8 | 2.38516 | 248 |
| 38.563 | 7.7 | 2.33274 | 162 |

Example 3B. Form III of Meglumine Salt Form

Preparation of dihydrate: About 60 mg of meglumine salt (Form I) was dissolved in 3 mL of methanol with stirring at 60° C. Added 6 mL of water and kept stirring for 30 min at 60° C. The clear solution was cooled slowly to room temperature and kept stirring at room temperature overnight. No precipitation occurred. Added 1 mL of water and stirred overnight again, solid sample appeared and was collected by filtration. After drying at 40° C. for 4 h, XRPD showed that most of the sample became anhydrous (Form II). Stirred in water for 30 min and dried at room temperature, dihydrate was prepared.

Alternatively, the dihydrate form can be prepared by using solvent/antisolvent precipitation method. For example, about 20 mg of meglumine salt was dissolved in 1 mL of methanol with stirring at 60° C. Added 2 mL of water, and kept stirring at 60° C. for 20 min. Cooled slowly to room temperature. The solution is clear at first. Precipitation occurred after stirred at room temperature overnight. The crystalline form obtained from this precipitation is dihydrate.

The sample was tested by XRPD, TGA and DSC. There was about 6.824% weight loss prior to decomposition. In DSC profile, there were two endothermic peaks with onset temperature of 63.4° C. and 176.4° C., respectively.

Characterization of Dihydrate: Representative XRPD and DSC spectra are shown in FIGS. 3A-3B. A table of XRPD peaks are shown below in Table 2.

TABLE 2

Table of XRPD Peaks for Dihydrate Meglumine Salt

| Angle 2-Theta ° | Intensity % % | d value Angstrom | Intensity Count |
|---|---|---|---|
| 3.682 | 46.2 | 23.9776 | 549 |
| 6.401 | 23.4 | 13.79821 | 278 |
| 7.46 | 46.4 | 11.84147 | 551 |
| 10.245 | 68.5 | 8.62762 | 814 |
| 11.216 | 22.7 | 7.88285 | 270 |
| 11.969 | 51.3 | 7.38831 | 609 |
| 14.463 | 100 | 6.11939 | 1188 |
| 14.975 | 14.6 | 5.91139 | 173 |
| 15.552 | 37.5 | 5.69327 | 446 |
| 16.691 | 16.7 | 5.3072 | 198 |
| 16.968 | 31.3 | 5.22105 | 372 |
| 17.357 | 51.5 | 5.10515 | 612 |
| 17.777 | 26.8 | 4.98523 | 318 |
| 18.751 | 12.6 | 4.72849 | 150 |
| 19.181 | 51.7 | 4.62345 | 614 |
| 19.714 | 39.4 | 4.49964 | 468 |
| 20.294 | 27.5 | 4.3723 | 327 |
| 20.559 | 49.3 | 4.31661 | 586 |
| 21.084 | 17.3 | 4.21037 | 205 |
| 21.542 | 31.2 | 4.12184 | 371 |
| 21.967 | 97.2 | 4.04296 | 1155 |
| 22.501 | 50.3 | 3.94828 | 597 |
| 22.794 | 21.5 | 3.8982 | 255 |
| 23.761 | 37 | 3.74163 | 439 |
| 24.606 | 46.5 | 3.615 | 552 |
| 24.946 | 32 | 3.56653 | 380 |
| 25.503 | 20.7 | 3.48992 | 246 |
| 25.876 | 22.3 | 3.44047 | 265 |
| 26.501 | 21.7 | 3.36075 | 258 |
| 27.65 | 14.1 | 3.2236 | 168 |
| 28.078 | 30.8 | 3.17543 | 366 |
| 28.96 | 14.7 | 3.08069 | 175 |
| 29.792 | 13 | 2.99655 | 155 |
| 30.134 | 15.2 | 2.96333 | 181 |
| 30.851 | 22.4 | 2.89604 | 266 |
| 31.433 | 21.4 | 2.84373 | 254 |
| 32.22 | 14.1 | 2.776 | 168 |
| 32.853 | 15.7 | 2.724 | 187 |
| 33.07 | 18.9 | 2.70662 | 225 |
| 35.162 | 15.1 | 2.55018 | 179 |
| 35.587 | 19.4 | 2.52074 | 231 |
| 37.364 | 12 | 2.40479 | 143 |
| 38.134 | 16.8 | 2.35803 | 200 |
| 39.32 | 15.9 | 2.28955 | 189 |

Example 3. Form II of the Meglumine Salt

Preparation of Form II: The dihydrate prepared above was dried at 60° C. for 5 h and 40° C. overnight. The sample was tested by XRPD, TGA and DSC immediately. XRPD pattern of the dry sample was different from Form I and dihydrate (FIG. 2A). Determined by TGA and DSC, there were no weight loss prior to decomposition, and two endothermic peaks in DSC profile (FIG. 2B). The melting of sample was 174.13° C. The small endothermic peak with onset temperature of 43.41 and enthalpy of 3.999 J/g should be the peak of desolvation. Little water should be adsorbed during DSC testing. The sample with the melting of 174.13° C. was named as Form II. The sample was used for interconversion studies.

Characterization of Form II: Representative XRPD and DSC spectra are shown in FIGS. 2A-2B. A table of XRPD peaks are shown below in Table 3.

TABLE 3

XRPD Peaks for Form II

| Angle 2-Theta ° | Intensity % % | d value Angstrom | Intensity Count |
|---|---|---|---|
| 3.997 | 34.8 | 22.08663 | 577 |
| 7.569 | 16.1 | 11.67003 | 267 |
| 7.983 | 87.7 | 11.0666 | 1456 |
| 10.257 | 24.2 | 8.61696 | 402 |
| 11.247 | 13.8 | 7.86115 | 229 |
| 11.956 | 83.5 | 7.39632 | 1386 |
| 12.351 | 46.3 | 7.16088 | 769 |
| 13.095 | 15.1 | 6.75554 | 250 |
| 14.666 | 28.2 | 6.03523 | 468 |
| 14.896 | 20.7 | 5.94248 | 344 |
| 15.541 | 27.2 | 5.69708 | 451 |
| 16.145 | 37.3 | 5.48558 | 619 |
| 17.22 | 34 | 5.14533 | 564 |
| 17.791 | 9.2 | 4.98143 | 153 |
| 18.544 | 12.8 | 4.78076 | 213 |
| 18.944 | 15.2 | 4.68083 | 253 |
| 19.327 | 17.5 | 4.58881 | 290 |
| 19.653 | 43.4 | 4.51344 | 720 |
| 19.938 | 19.4 | 4.44964 | 322 |
| 20.515 | 17 | 4.32574 | 283 |
| 20.831 | 26.1 | 4.26092 | 433 |
| 22.072 | 40.2 | 4.02395 | 667 |
| 22.528 | 100 | 3.94362 | 1660 |
| 23.235 | 13.9 | 3.82509 | 230 |
| 23.885 | 33.4 | 3.72254 | 554 |
| 24.527 | 19.5 | 3.62652 | 324 |
| 24.836 | 20.2 | 3.58213 | 336 |
| 25.695 | 12.5 | 3.4643 | 208 |
| 26.285 | 22.3 | 3.38783 | 371 |
| 27.049 | 10.8 | 3.29385 | 179 |
| 28.003 | 16.3 | 3.18375 | 270 |
| 29.16 | 12.7 | 3.06002 | 210 |
| 29.549 | 10.7 | 3.02064 | 177 |
| 30.185 | 9.9 | 2.9584 | 165 |
| 30.707 | 19 | 2.90925 | 316 |
| 32.769 | 18.1 | 2.73077 | 301 |
| 33.724 | 10.2 | 2.6556 | 170 |
| 34.299 | 9.8 | 2.61235 | 163 |
| 35.256 | 12 | 2.54361 | 200 |
| 35.458 | 10.5 | 2.5296 | 174 |
| 37.221 | 10.9 | 2.41372 | 181 |
| 38.178 | 11.4 | 2.3554 | 190 |
| 39.46 | 10.2 | 2.28177 | 170 |

Example 3D. Meglumine Salt Form Interconversion Study

Interconversion study: Interconversion studies were carried out by mixing the same amount of different form solids in IPA or water, respectively. Suspensions were kept stirring at room temperature and 60° C. for several days, during which suspensions were filtrated and analyzed by XRPD.

Eight conditions with different substances, temperature and solvents were used for interconversion study. Results showed that dihydrate was the most stable crystal form in water at room temperature, and Form I was the most stable crystal form in water at 60° C. and IPA.

All conditions and results were listed in Table 4.

TABLE 4

| Results of interconversion study. | | | |
|---|---|---|---|
| Substances | Solvent | Temperature | Final crystal form |
| Form I, Dihydrate | Water | 25° C. | Dihydrate |
| | | 60° C. | Form I |
| | IPA | 25° C. | Form I |
| | | 60° C. | Form I |
| Form I, | Water | 25° C. | Dihydrate |
| Form II, Dihydrate | IPA | 25° C. | Form I |
| Form I | Water | 25° C. | Dihydrate |
| Form I | Water | 60° C. | Form I |

Example 3E. Meglumine Salt Form Stability Study

Solid stability test of Form I at 92.5% RH for 10 days: About 20 mg of meglumine salt Form I was put into the condition of 25° C./92.5% RH for 10 days. At 10 days, the sample was analyzed by XRPD.

Figure 1C:
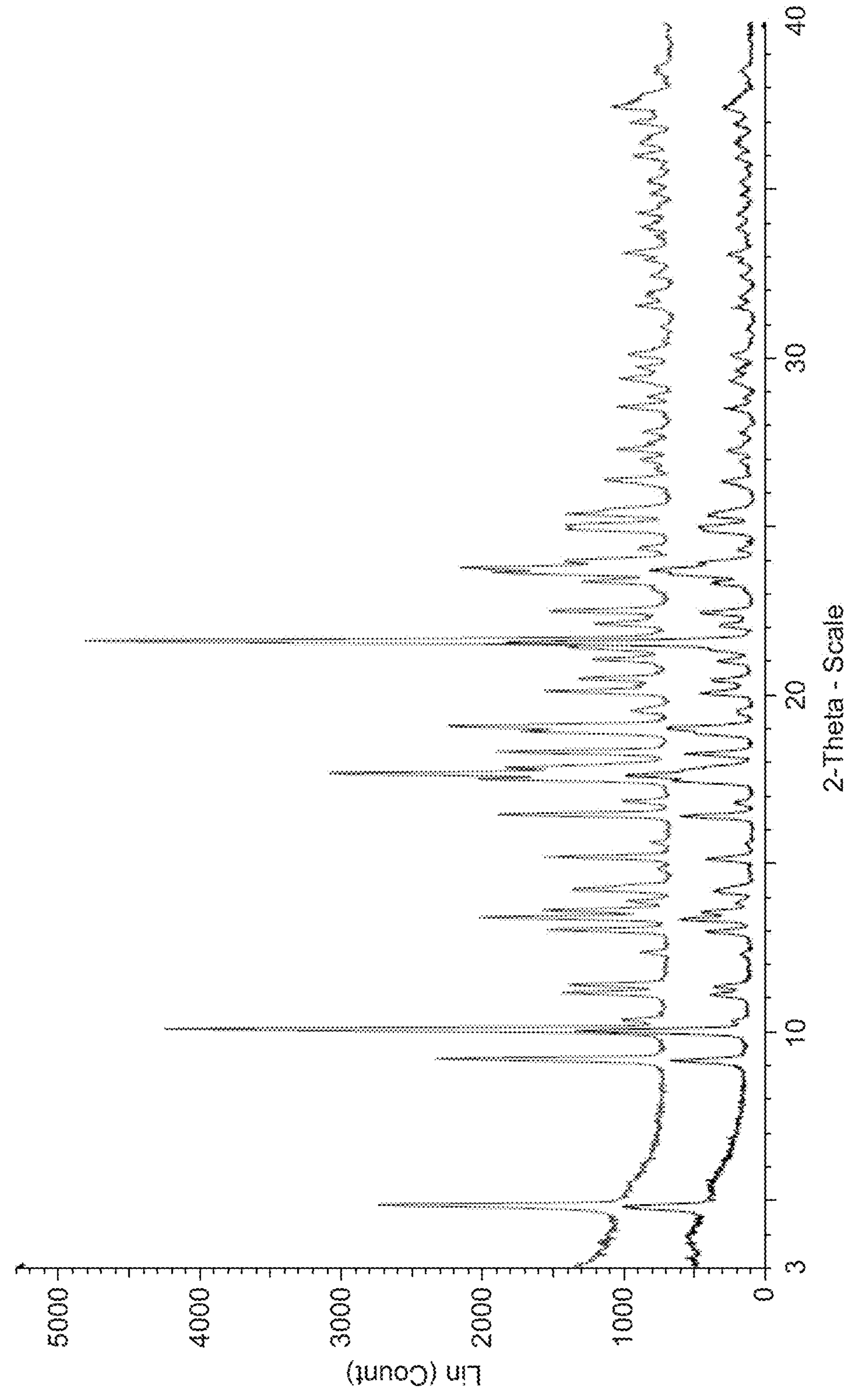

Result showed that the Form I of meglumine salt remained unchanged after 10 days. Representative XRPD patterns were shown in FIG. 1C.

Conclusion Meglumine salt of Compound FA solid state was prepared and used as initial material (Form I) for polymorph screening. Two crystal forms (Form I, II) and dihydrate were identified and prepared in the screening. Interconversion studies of different forms and dihydate were performed in water and IPA at room temperature or 60° C. Results showed that dihydrate was the most stable in water at room temperature, and Form I was the most stable in IPA (room temperature and 60° C.) and in water at 60° C. In addition, Form I of meglumine salt remained unchanged after storage at 92.5% RH for 10 days.

Example 4. Preparation of L-Lysine Salt and Meglumine Salt for Solubility and Stability Test Lysine Salt: 239.8 mg of Compound FA was dissolved in 4.5 mL of isobutanol at 50° C. with stirring. 0.52 mL of 1 M L-lysine/water solution was added. Precipitation occurred about 15 min later. The reaction was kept stirring at 50° C. for about 1 hour. Cooled to room temperature, the solid sample was collected by filtration and dry under vacuum at 60° C. overnight. This lysine salt obtained is Form A. Representative XRPD and DSC spectra are shown in FIGS. 4A-4B. A table of XRPD peaks are shown below in Table 5.

TABLE 5

| XRPD peaks of L-lysine salt in Form A | | | |
|---|---|---|---|
| Angle 2-Theta ° | Intensity % % | d value Angstrom | Intensity Count |
| 4.172 | 46.4 | 21.16375 | 982 |
| 8.357 | 14.4 | 10.57154 | 304 |
| 10.151 | 100 | 8.70741 | 2117 |
| 11.06 | 29 | 7.99305 | 613 |
| 12.525 | 19.1 | 7.06178 | 405 |
| 13.007 | 49.5 | 6.80083 | 1047 |
| 13.301 | 20.2 | 6.65135 | 428 |
| 14.6 | 15.8 | 6.06208 | 335 |
| 15.128 | 7.7 | 5.85202 | 163 |
| 15.963 | 10.1 | 5.54746 | 214 |
| 16.33 | 11.9 | 5.42356 | 252 |
| 16.688 | 7.8 | 5.30809 | 165 |

TABLE 5-continued

| XRPD peaks of L-lysine salt in Form A | | | |
|---|---|---|---|
| Angle 2-Theta ° | Intensity % % | d value Angstrom | Intensity Count |
| 16.964 | 10.6 | 5.22235 | 224 |
| 19.111 | 12 | 4.64034 | 255 |
| 19.404 | 48.1 | 4.57085 | 1018 |
| 20.383 | 18.2 | 4.35342 | 386 |
| 20.896 | 44.6 | 4.24784 | 944 |
| 22.231 | 37 | 3.99555 | 783 |
| 22.427 | 31.7 | 3.96111 | 671 |
| 22.948 | 67.7 | 3.87243 | 1434 |
| 23.428 | 15.3 | 3.79408 | 324 |
| 24.612 | 19.8 | 3.61413 | 419 |
| 26.451 | 11 | 3.36687 | 233 |
| 26.757 | 7.2 | 3.32907 | 152 |
| 27.422 | 5.5 | 3.24985 | 117 |
| 28.811 | 10.6 | 3.09629 | 225 |
| 29.442 | 7 | 3.03135 | 148 |
| 29.733 | 7.7 | 3.0023 | 162 |
| 30.754 | 10 | 2.90496 | 211 |
| 31.72 | 22.8 | 2.8186 | 483 |
| 32.203 | 7.3 | 2.77742 | 154 |
| 32.598 | 8.5 | 2.74471 | 179 |
| 32.731 | 8.7 | 2.73387 | 185 |
| 33.038 | 10.3 | 2.70915 | 219 |
| 33.799 | 7.7 | 2.64987 | 163 |
| 35.15 | 5.4 | 2.55105 | 114 |
| 35.545 | 5.4 | 2.52357 | 115 |
| 36.475 | 8.1 | 2.46133 | 171 |
| 37.212 | 5.7 | 2.41431 | 120 |
| 37.717 | 5.8 | 2.38309 | 123 |

Meglumine Salt: 237.92 mg of Compound FA was dissolved in 5 mL of IPA at room temperature with stirring. Then 10 mL of 0.05 M meglumine/methanol solution was added. Precipitation occurred about 25 min later. The reaction was kept stirring at room temperature for 3 hours. The solid sample was obtained by filtration and dry under vacuum at 60° C. overnight. Analysis shows that the meglumine salt obtained is Form I.

For solubility test: About 20 mg of Compound FA, L-lysine salt and meglumine salt (Form I) were weighed into vials, added 3 mL of pH1.2 or pH 6.8 buffer to make saturated solutions. All suspensions were kept shaking with 200 rpm at room temperature for up to 24 hours. At 30 min and 24 hours, the sample solution was filtered and analyzed by HPLC to determine the solubility. At 24 hours, remaining solids were collected and determined by XRPD.

For stability test: About 20 mg of Compound FA, L-lysine salt and meglumine salt (Form I) were weighed into vials, and put at the condition of 40° C./75% RH for 8 days. At 0 and 8 days, the solid sample was dissolved using acetonitrile/water (1/1) to make a solution with the concentration of 0.2 mg/mL. Sample solutions were analyzed by HPLC and solid samples were examined by XRPD.

Results of Solubility Test

The solubility of Compound FA, L-lysine salt and meglumine salt was tested in pH 1.2 and pH 6.8 buffer solutions at 30 min and 24 h. The remaining solid samples at 24 hours were analyzed by XRPD. HPLC results showed that the three samples tested were unstable in pH 1.2 buffer solution.

The solubility was calculated with the sum of impurities and major peak area. All solubility results were listed in Table 6. The two salts tested showed much higher solubility than Compound FA at 30 min and 24 hours. XRPD analysis show that L-lysine salt changed to amorphous, while crystallinity of Compound FA and meglumine salt became lower. Based on $^{1}H$ NMR analysis, degradation occurred in pH 1.2 buffer and dissociation appeared in pH6.8 buffer.

TABLE 6

Solubility of Lysine Salt, Meglumine salt and Compound FA

| Sample | Media | Solubility at 30 min (mg/mL) | Solubility at 24 h (mg/mL) | XRPD patterns at 24 h |
|---|---|---|---|---|
| Compound FA | pH 1.2 | 0.571 | 0.267 | Low crystallinity |
| | pH 6.8 | 0.014 | 0.003 | Low crystallinity |
| Meglumine salt | pH 1.2 | 0.296 | 1.612 | No change |
| | pH 6.8 | 0.020 | 0.017 | Low crystallinity |
| L-lysine salt | pH 1.2 | 0.387 | 1.343 | Amorphous |
| | pH 6.8 | 0.017 | 0.019 | Amorphous |

The solubility in pH1.2 was calculated with the sum of impurities and major peak area.

Results of Solid Stability Test

After storage at 40° C./75% RH for 8 days, solid stability test of Compound FA, L-lysine salt and meglumine salt was determined by HPLC and XRPD. HPLC results (Table 7) showed that no obvious degradation occurred, and the purity of the two tested salts was higher. XRPD patterns were not changed after storage at 40° C./75% RH for 8 days. Compound FA, L-lysine salt and meglumine salt were all physically and chemically stable at 40° C./75% RH for 8 days.

TABLE 7

Stability of Lysine Salt, Meglumine salt and Compound FA

| Sample | Purity at 0 day (Area %) | Purity at 8 days (Area %) |
|---|---|---|
| Compound FA | 98.02 | 96.31 |
| Meglumine salt | 99.68 | 99.66 |
| L-lysine salt | 99.77 | 99.66 |

CONCLUSION

Crystalline L-lysine salt and meglumine salt (dihydrate and anhydride) were successfully prepared and characterized by $^1H$ NMR, XRPD, DSC, TGA and DVS. By comparing solid state characteristics of each salt, L-lysine salt (Form A) and anhydrous meglumine salt (Form I) were selected for further evaluation along with free acid by solubility/solid stability testing.

In solubility testing, the two salts showed much higher solubility than Compound FA at 30 min and 24 hours. Compound FA and the salts were all degraded in pH 1.2 buffer. In solid stability evaluation, L-lysine salt and meglumine salt were both physically and chemically stable at 40° C./75% RH for 8 days. Their purity was higher than Compound FA.

Example 5A. Preparation of 10 and 50 mg Strength Tablets

This example shows preparation of two different strength tablets (10 mg and 50 mg). Tablets of other strengths can be prepared by following this example similarly. Both tablets are formulated for immediate release and can be contained in common container closure systems such as high density polyethylene (HDPE) bottles with polypropylene (PP) caps.

Meglumine salt of Compound FA: the active ingredient (prepared according to Example 2, form I) was micronized. The active ingredient was found to have a bulk density of about 0.238 g/ml and tap density of about 0.359 g/ml. The particle size distribution of the meglumine salt was analyzed with a Malvern laser particle size analyzer. Detection method: Use Microtrac's S3500 laser particle size analyzer equipped with SDC (injection, transmission, control) sampling system to detect particle size distribution. Using a wet test, the sample was dispersed in Isopar G isoparaffinic solvent. Sonicate for 30 seconds to reduce potential agglomeration. In one batch tested, the D90 of this material was found to be less than 20 μm. See below:

| Sonication time | D10 (μm) | D50 (μm) | D90 (μm) |
|---|---|---|---|
| 0 | 2.57 | 5.35 | 10.98 |
| 30 seconds | 2.52 | 5.37 | 11.08 |

Formulation detail: Table 8A shows representative ingredients of the 50 mg tablets. The 10 mg strength tablets have the same ingredients and weight percentages, except that they are based on 10 mg of active ingredients.

TABLE 8A

Ingredients for 50 mg strength Tablet

| Ingredients | Theoretical Unit Formula (mg) | Content (w/w %) | Function |
|---|---|---|---|
| Meglumine salt of Compound FA* | 70.532 | 17.633 | Drug substance |
| Sodium Lauryl Sulfate Fine | 20.000 | 5.000 | Surfactant |
| Microcrystalline Cellulose PH-101 | 80.000 | 20.000 | Diluent |
| Mannitol 50C | 189.468 | 47.367 | Diluent |
| Povidone K30 | 12.000 | 3.000 | Binder |
| Croscarmellose sodium | 24.000 | 6.000 | Disintegrant |
| Sodium stearyl fumarate | 4.00 | 1.00 | Lubricant |
| Core tablet weight | 400.00 | 100.00 | N/A |
| Opadry II 85G68918 | 20.000 | 5.000** | Coating Material |
| Total | 420.00 | N/A | N/A |

*Product dosage strength is based on free acid, and conversion factor is 1.4107. 50 mg free acid equals 70.53 mg meglumine salt.

**5.00% coating weight gain is w/w % to core tablet weight.

Formulation Process: the tablets were prepared using wet granulation to provide granules, which were then compressed into the 10 mg or 50 mg strength tablets. The drug substance, microcrystalline cellulose PH101, mannitol 50C, sodium lauryl sulfate, croscarmellose sodium (intra-granular addition), povidone K30 were passed through a 30 mesh sieve. The mixture was pre-blended in the wet granulator for at least 3 minutes. Set a high-efficiency wet granulator with a stirring speed of 450 rpm and a chopping speed of 1500 rpm, add a theoretical amount of povidone solution within 3 minutes, and add an appropriate amount of water according to the state of the particles. After the addition of the povidone solution, granulation process was carried out for about 1-3 minutes to provide wet granules. The effect of three different granulation durations (1 minute, 2 minutes, and 3 minutes) on the dissolution of the 50 mg tablets was studied. The dissolution data at 30 min indicated that granulation durations had no significant effect on dissolution of the tested 50 mg tablets, all tested tablets had greater than 95% drug release at 30 minutes.

The wet granules were then transferred for drying using a fluidized bed at about 40-50° C. until the moisture content (LOD) is not more than 3%. The dried granules were passed through a 30 mesh sieve, and the granules above the 30 mesh sieve were crushed. Then croscarmellose sodium was passed through a 30-mesh sieve to the mixer barrel and mixed with the dried granules at 20 rpm for 10 minutes. Sodium stearyl fumarate was then passed through a 30 mesh sieve to the mixing tank and mixed with the material at 20 rpm for 5 min. The mixture thus formed was found to be homogenous.

The above mixture was then compressed into 10 mg tablets, each of which weigh about 80 mg with a diameter of about 6 mm and a thickness of about 2.6 mm, or 50 mg tablets, each of which has a weight of about 400 mg, with a diameter of 10 mm and a thickness of about 4.8 mm. The hardness of the tablets has little effect on dissolution using the paddle method at 50 rpm, 900 ml medium, which can be 0.5% SDS in water. For 10 mg tablets, tablets with hardness in the range of 20-40 N have similar dissolution. For 50 mg tablets, tablets with hardness in the range of 35-80 N have similar dissolution.

The 10 mg tablets or 50 mg tablets prepared above were then coated with Opadry II 85G68918. For these tablets, different coating weight gains had no significant effect on dissolution (from 0 to 3.5%) using the paddle method at 50 rpm, 900 ml medium, which can be 0.5% SDS in water.

The coated tablets were packed in high-density polyethylene bottles with moisture-proof caps, and then used aluminum foil bags as secondary packaging.

Dissolution Test: the tablets prepared can be tested for dissolution using the paddle method (Chinese Pharmacopoeia <0931>, method 2, paddle) at 50 rpm, 900 ml medium, which can be 0.5% SDS in water. The 10 mg and 50 mg strength tablets prepared in this example were found to have about 80% or above drug released at about 45 minutes and almost 100% at 60 minutes.

Beagle dog PK studies: a dog PK study was carried out to compare the PK profile of a 50 mg strength tablet prepared in this example with those of Compound FA oral suspension. As shown in Table 8B, the PK study indicated that the addition of about 5% SDS in the tablet achieved similar plasma levels of Compound FA with the oral suspension formulation at 1 hr, 2 hr, 4 hr, 6 hr, 8 hr, and 24 hrs. The tablet with 5% SDS also achieved higher plasma concentrations at 1 hr, 2 hr, 4 hr, 6 hr, 8 hr, and 24 hrs than the tablet formulation without the 5% SDS, which formulation is the same as the 50 mg tablet formulation shown in Table 8A, except that the 5% SDS is replaced with 5% mannitol.

TABLE 8B

Beagle Dog Pharmacokinetic Study Results

| Formulation | Time Point | Plasma Concentration of Compound FA (ng/mL) 10 min | 30 min | 1 hr | 2 hr | 4 hr | 6 hr | 8 hr | 24 hr |
|---|---|---|---|---|---|---|---|---|---|
| Oral Suspension | N | 6 | 6 | 6 | 6 | 6 | 6 | 6 | 6 |
| of Compound FA | mean | 3515 | 9343 | 12880 | 16683 | 18233 | 16183 | 14550 | 5670 |
| | SD | 1400 | 3430 | 3507 | 4778 | 3689 | 2759 | 2534 | 1188 |
| | CV(%) | 39.8 | 36.7 | 27.2 | 28.6 | 20.2 | 17.1 | 17.4 | 20.9 |
| 50 mg strength | N | 6 | 6 | 6 | 6 | 6 | 6 | 6 | 6 |
| tablet without | mean | 1347 | 4683 | 6823 | 9057 | 9972 | 9810 | 8758 | 4277 |
| 5% SDS | SD | 1104 | 1982 | 3541 | 4753 | 5403 | 5067 | 4744 | 2025 |
| | CV(%) | 82.0 | 42.3 | 51.9 | 52.5 | 54.2 | 51.6 | 54.2 | 47.4 |
| 50 mg strength | N | 6 | 6 | 6 | 6 | 6 | 6 | 6 | 6 |
| tablet with 5% | mean | 57.4 | 2750 | 8157 | 13905 | 16883 | 16500 | 15467 | 8453 |
| SDS | SD | 50.8 | 3094 | 6580 | 5318 | 4442 | 3114 | 3028 | 1614 |
| | CV(%) | 88.5 | 113 | 80.7 | 38.2 | 26.3 | 18.9 | 19.6 | 19.1. |

Example 5B. Preparation of 100 mg and 200 mg Strength Tablets

This example shows preparation of tablets of two different strengths (100 mg and 200 mg). Tablets with other strengths can be prepared by following this example similarly. The 100 mg tablet has a core weight of about 400 mg, coated with a yellow coating layer. The 200 mg tablet has a core weight of about 600 mg, also coated with a yellow coating layer. Both tablets are formulated for immediate release and can be contained in common container closure systems such as high density polyethylene (HIDPE) bottles with polypropylene (PP) caps.

Formulation details: Tables 8C and 8D show representative ingredients of the 100 mg and 200 mg tablets.

TABLE 8C

Ingredients for 100 mg strength Tablet

| Ingredients | Theoretical Unit Formula (mg) | Content (w/w %) | Function |
|---|---|---|---|
| Intra-granular | | | |
| Meglumine salt of Compound FA* | 141.07 | 35.27 | Drug substance |
| Sodium Lauryl Sulfate Fine | 20.00 | 5.00 | Surfactant |
| Microcrystalline Cellulose PH-101 | 67.65 | 16.91 | Diluent |
| Mannitol 50C | 135.28 | 33.82 | Diluent |
| Povidone K30 | 8.00 | 2.00 | Binder |
| Crospovidone XL-10 | 12.00 | 3.00 | Disintegrant |
| Extra-granular | | | |
| Crospovidone XL-10 | 12.00 | 3.00 | Disintegrant |
| Magnesium stearate 5712 | 4.00 | 1.00 | Lubricant |
| Core tablet weight | 400.00 | 100.00 | N/A |
| Purified Water (for Granulation)** | 95.08 | 24.76 | Solvent |
| Opadry II 85F620077-CN Yellow*** | 12.00 | 3.00 | Coating Material |
| Purified Water (for Coating) | N/A | N/A | Solvent |
| Total | 412.00 | N/A | N/A |

*Product dosage strength is based on free acid, and conversion factor is 1.4107. 100 mg free acid equals 141.07 mg meglumine salt.
**24.76% is w/w % to intra-granular excipients. Purified water is removed during drying process, and its quantity will not be calculated in total material quantity.
***3.00% coating weight gain is w/w % to core tablet weight. The Opadry components are the following: polyvinyl alcohol, titanium dioxide, polyethylene glycol, talc powder, and yellow iron oxide.

TABLE 8D

| Ingredients for 200 mg strength Tablet | | | |
|---|---|---|---|
| Ingredients | Theoretical Unit Formula (mg) | Content (w/w %) | Function |
| Intra-granular | | | |
| Meglumine salt of Compound FA* | 282.14 | 47.02 | Drug substance |
| Sodium Lauryl Sulfate Fine | 30.00 | 5.00 | Surfactant |
| Microcrystalline Cellulose PH-101 | 110.93 | 18.49 | Diluent |
| Mannitol 50C | 110.93 | 18.49 | Diluent |
| Povidone K30 | 24.00 | 4.00 | Binder |
| Crospovidone XL-10 | 18.00 | 3.00 | Disintegrant |
| Extra-granular | | | |
| Crospovidone XL-10 | 18.00 | 3.00 | Disintegrant |
| Magnesium stearate 5712 | 6.00 | 1.00 | Lubricant |
| Core tablet weight | 600.00 | 100.00 | N/A |
| Purified Water (for Granulation)** | 134.61 | 23.37 | Solvent |
| Opadry II 85F620077-CN Yellow*** | 18.00 | 3.00 | Coating Material |
| Purified Water (for Coating) | N/A | N/A | Solvent |
| Total | 618.00 | N/A | N/A |

*Product dosage strength is based on free acid, and conversion factor is 1.4107. 200 mg free acid equals 282.14 mg meglumine salt.
**23.37% is w/w % to intra-granular excipients. Purified water is removed during drying process, its quantity will not be calculated in total material quantity.
***3.00% coating weight gain is w/w % to core tablet weight.

Process Description: Use 30 mesh screen to sieve the following materials into the Granulation Bowl, sequentially, Mannitol 50C, Crospovitone XL-10 (intra-granular), Povidone K30, Meglumine salt of Compound FA (form I, micronized), Sodium Lauryl Sulfate, and Microcrystalline Cellulose PH-101. The mixture was then wet granulated with a High Shear Granulator (TMG1/6, Glatt), which includes pre-blending, spraying, and then granulation to provide wet granules. The wet granules were then dried using fluid-bed drying, (GPCG 2, Glatt), typically the water content of dried granules was controlled to be no greater then 3%. The dried granules were then dry milled using Comil U5 (Quadro) with a 991 μm sieve. After which, the dry milled granules were blended with Crospovidone XL-10 (extra-granule), which was screened using 30 mesh sieve, and magnesium stearate, also screened using 30 mesh sieve. This mixture was then compressed into tablets using a rotary tablet press method, XL-100 (Korsch), to provide the desired tablets. The ingredients and amounts used in the process to produce the 100 mg and 200 mg strength tablets are detailed in Tables 8C and 8D, respectively. The Tablet Press parameters at Setup can be adjusted to achieve a thickness of about 5.50 (about 5.30-5.70) mm; hardness of about 10.00 (about 8.00-14.00) KP; disintegration Time≤10 min. For the 100 mg strength tablet, the total tablet core weights about 400 mg. For the 200 mg strength tablet, the total tablet core weights about 600 mg. The tablet core produced was then coated with Opadry II 85F620077-CN Yellow, with a target weight gain of about 3% (e.g., about 2.5-3.5%). The coated tablets can be packaged in HDPE bottles with PP caps.

Stability: Good chemical and physical stability of the 100 mg strength Tablets (exposed and bottle packaged tablet) were shown when stored under the conditions of 60° C., 25° C./92.5% RH, 40° C./75% RH and light ($1.2\times10^6$ Lux hr/200 w hr/m2). There was no significant change in appearance, assay and related substance in 30 days, when compared to initial. It was observed from results of water content, that bulk tablets gained more moisture after 10 days and 30 days storage under the condition of 25° C./92.5% RH and 40° C./75% RH, when compared to tablets packaged in bottle. Similarly, Good chemical and physical stability of the 200 mg strength Tablets (exposed and bottle packaged tablet) were shown when stored under the condition of 60° C., 25° C./92.5% RH, 40° C./75% RH and light ($1.2\times10^6$ Lux hr/200 w hr/m2) for both exposed and packaged tablet. Water content was increase to some extent when stored at 25° C./92.5% RH. There was no significant change in appearance, assay and related substance in 30 days, when compared to initial.

During the process development of the 100 mg strength tablets, it was found that the ratio of microcrystalline cellulose and mannitol can have an impact on dissolution (see details of dissolution test in Example 5A). Specifically, when sodium croscarmellose is used as disintegrant, tablets with a weight ratio of microcrystalline cellulose to mannitol of about 1:2 had a faster dissolution at all tested time points (5 min, 15 min, 30 min, 45 min, 60 min, and 75 min), compared to that observed for tablets with the corresponding ratio of about 2:1. It was also found that the use of Crospovidone in the 100 mg strength tablet formulation is beneficial. Dissolution rates of tablets with three different disintegrants were compared, sodium croscarmellose, sodium carboxymethyl starch, and crospovidone. It was found that tablets with crospovidone had a faster disintegration (8 min) compared to that observed for tablets with sodium carboxymethyl starch (12 min) or sodium croscarmellose (10 min).

During the process development, it was also found that water amount and granulation time during the wet granulation process may have impact on granule micro structure which can further impact the tablet properties such as its dissolution. For wet granulation in 1L bowl, 25% water amount and 1-3 min granulation time were considered as suitable process parameters. The acceptable value of water amount and end point of granulation for different manufacturing scales may be adjusted based on granule morphology and texture.

Large size granules were observed during wet milling process. Therefore, to avoid potential risk of over-granulation, wet milling is preferably not included in the tablet manufacturing process. There was no significant impact of Loss on Drying (LOD) value on granule particle size distribution (PSD), tablets attributes or sticking issue, LOD was then set not more than 3%. For dry-milling, the mill screen size and speed were found to have no significant impact on granule PSD. For the processed used herein, the screen size of 991 m and a faster mill speed 1750 rpm were selected. The targeted disintegration time was set as not more than 10 min. Hardness of tablets was found to have no correlation with disintegration time and dissolution. Based on friability request and others, the hardness range described in this example for the 100 mg and 200 mg strength tablets was set to be about 8-14 KP or about 80 N to about 140 N.

Coating was found to have negative impact on tablet dissolution. Results of 3% and 5% coating weight gain on related substance under photostability testing demonstrate that the 200 mg strength coated tablet was stable under light condition ($1.2\times10^6$ Lux·hr/200 w hr/m2). There was no great increase of impurities for both coating gain. In addition, coated tablets with 3% and 5% weight gain showed no great difference in impurities. Balancing tablet dissolution and photostability testing result, for this example, a 3% coating weight gain was selected.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A pharmaceutical composition comprising a meglumine salt of Compound FA represented by the structure below:

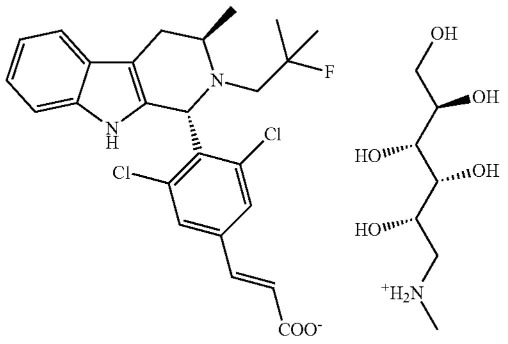

wherein the meglumine salt of Compound FA is in a crystalline Form I characterized by an X-ray powder diffraction (XRPD) pattern having the following peaks: 4.7, 9.1, 10.0, 17.6, 18.2, 19.0, 21.5, and 23.7 degrees 2 theta, ±0.2°, wherein the meglumine salt of Compound FA is in an amount equivalent to about 10 mg, about 20 mg, about 30 mg, about 40 mg, about 50 mg, about 75 mg, about 100 mg, about 150 mg, about 200 mg, about 250 mg, about 300 mg, about 400 mg, or about 500 mg of Compound FA.

2. The pharmaceutical composition of claim 1, which is in a unit dosage form.

3. A tablet comprising:

a) a meglumine salt of Compound FA in an amount of about 10% to about 80% by weight;

b) a surfactant in an amount of about 0.1% to about 10% by weight, c) a diluent in an amount of about 15% to about 70% by weight, d) a binder in an amount of about 0.1% to about 10% by weight, e) a disintegrant in an amount of about 0.1% to about 10% by weight, and f) a lubricant in an amount of about 0.1% to about 5% by weight, wherein the meglumine salt of Compound FA is represented by the structure below:

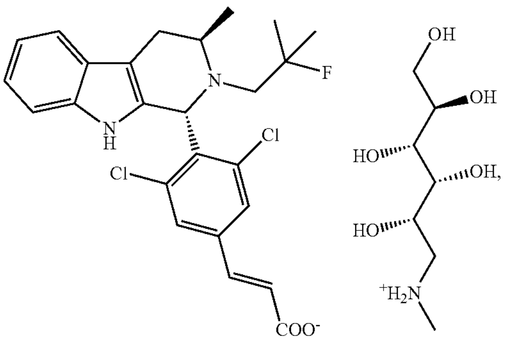

and wherein the meglumine salt of Compound FA is in a crystalline Form I characterized by an X-ray powder diffraction (XRPD) pattern having the following peaks: 4.7, 9.1, 10.0, 17.6, 18.2, 19.0, 21.5, and 23.7 degrees 2 theta, ±0.2°.

4. The tablet of claim 3, wherein the surfactant comprises sodium lauryl sulfate.

5. The tablet of claim 3, wherein the diluent comprises microcrystalline cellulose.

6. The tablet of claim 3, wherein the diluent comprises mannitol.

7. The tablet of claim 3, wherein the binder comprises a povidone.

8. The tablet of claim 3, wherein the disintegrant comprises crospovidone.

9. The tablet of claim 3, wherein the tablet further comprises a coating.

10. The tablet of claim 9, wherein the coating comprises polyvinyl alcohol.

11. The tablet of claim 9, wherein the coating weight gain is about 1% to about 5%.

12. A granule comprising a) a meglumine salt of Compound FA in an amount of about 10% to about 80% by weight;

b) a surfactant in an amount of about 0.1% to about 10% by weight, c) a diluent in an amount of about 15% to about 70% by weight, d) a binder in an amount of about 0.1% to about 10% by weight, and e) a disintegrant in an amount of about 0.1% to about 10% by weight, wherein the meglumine salt of Compound FA is represented by the structure below:

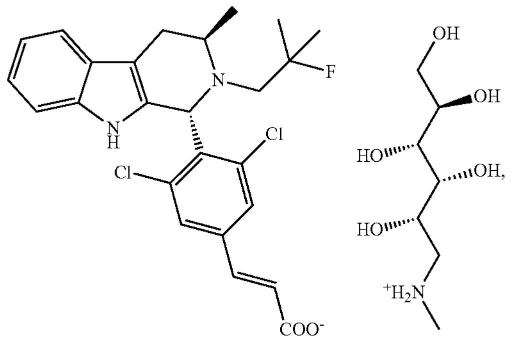

and wherein the meglumine salt of Compound FA is in a crystalline Form I characterized by an X-ray powder diffraction (XRPD) pattern having the following peaks: 4.7, 9.1, 10.0, 17.6, 18.2, 19.0, 21.5, and 23.7 degrees 2 theta, ±0.2°.

13. A process comprising:

a) wet granulating a mixture of a meglumine salt of Compound FA, surfactant, diluent, binder, and disintegrant to form wet granules;

b) optionally drying the wet granules to form dried granules; and c) optionally dry milling the dried granules to form dry milled granules, wherein the meglumine salt of Compound FA is represented by the structure below:

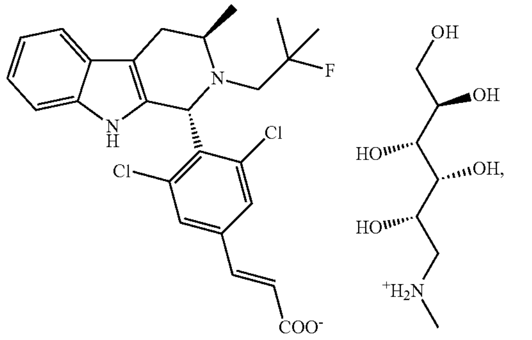

and wherein the meglumine salt of Compound FA in a crystalline Form I characterized by an X-ray powder diffraction (XRPD) pattern having the following peaks: 4.7, 9.1, 10.0, 17.6, 18.2, 19.0, 21.5, and 23.7 degrees 2 theta, ±0.2°.

14. The process of claim 13, further comprising blending the dry milled granules with an extra-granular disintegrant and a lubricant to form lubricated granules.

15. The process of claim 14, further comprising compressing the lubricated granules into a tablet core.

16. The process of claim 15, further comprising film coating the tablet core to form a coated tablet.

17. The process of claim 13, wherein the meglumine of Compound FA in the mixture is micronized and has a D90 of less than 500 μm.

18. The process of claim 17, wherein the meglumine of Compound FA in the mixture is micronized and has a D90 of less than 200 μm.

19. The process of claim 17, wherein the meglumine of Compound FA in the mixture is micronized and has a D90 of less than 20 μm.

20. A method of treating breast cancer, the method comprising administering to a subject in need thereof an effective amount of the pharmaceutical composition of claim 1.

* * * * *